(12) United States Patent
Hastings et al.

(10) Patent No.: US 11,452,448 B2
(45) Date of Patent: *Sep. 27, 2022

(54) SYSTEM, DEVICE, AND METHOD FOR DETERMINATION OF INTRAOCULAR PRESSURE

(71) Applicants: IOPtic, Inc., Lexington, KY (US); University of Kentucky Research Foundation, Lexington, KY (US)

(72) Inventors: Jeffrey Todd Hastings, Lexington, KY (US); E. Britt Brockman, Prospect, KY (US); Ingrid L. St. Omer, Lexington, KY (US); John C. Wright, Louisville, KY (US)

(73) Assignees: UNIVERSITY OF KENTUCKY RESEARCH FOUNDATION, Lexington, KY (US); IOPTIC, INC., Lexington, KY (US)

( * ) Notice: Subject to any disclaimer, the term of this patent is extended or adjusted under 35 U.S.C. 154(b) by 870 days.

This patent is subject to a terminal disclaimer.

(21) Appl. No.: 16/058,361

(22) Filed: Aug. 8, 2018

(65) Prior Publication Data

US 2018/0344158 A1 Dec. 6, 2018

Related U.S. Application Data

(62) Division of application No. 12/982,110, filed on Dec. 30, 2010, now Pat. No. 10,687,704.

(Continued)

(51) Int. Cl.
*A61B 3/16* (2006.01)

(52) U.S. Cl.
CPC .................................. *A61B 3/165* (2013.01)

(58) Field of Classification Search
CPC ......... A61B 3/16; A61B 3/165; G01L 9/0077; G01L 9/0079; Y10S 359/902
See application file for complete search history.

(56) References Cited

U.S. PATENT DOCUMENTS

| 4,428,239 A | * | 1/1984 | Johnston | ............... | G01L 9/0077 |
| | | | | | 356/482 |
| 4,926,696 A | * | 5/1990 | Haritonidis | ........... | G01L 9/0079 |
| | | | | | 250/231.19 |

(Continued)

*Primary Examiner* — Devin B Henson
*Assistant Examiner* — H. Q. Nguyen
(74) *Attorney, Agent, or Firm* — Jeffrey A. Haeberlin; Stites & Harbison, PLLC

(57) ABSTRACT

A system for determination of intraocular pressure includes: an intraocular pressure sensor; a light source illuminating the sensor with one or more wavelengths of light; and a detector that measures emitted light from the sensor. The sensor includes a substrate member, a spacer member, and a flexible membrane, which define a sealed cavity. The flexible membrane moves in response to intraocular pressure changes. A device for measuring intraocular pressure includes: the sensor; an anchoring member attached to the sensor for immobilizing the sensor in an eye; and a protective member attached to the anchoring member and covering the sensor to prevent contact between the flexible membrane and the eye. A method for determination of intraocular pressure includes: placing the sensor in an eye; illuminating, with a light source, the sensor with one or more wavelengths of light; and detecting, with a detector, a resultant light that contains information about intraocular pressure.

20 Claims, 14 Drawing Sheets

Related U.S. Application Data

(60) Provisional application No. 61/291,131, filed on Dec. 30, 2009.

(56) References Cited

U.S. PATENT DOCUMENTS

| | | | | |
|---|---|---|---|---|
| 5,956,142 | A * | 9/1999 | Muller | G01B 11/0683 356/504 |
| 6,193,656 | B1 * | 2/2001 | Jeffries | A61B 3/16 600/398 |
| 2002/0109851 | A1 * | 8/2002 | Deck | G01B 9/02004 356/512 |
| 2003/0078487 | A1 * | 4/2003 | Jeffries | A61B 3/16 600/398 |

* cited by examiner

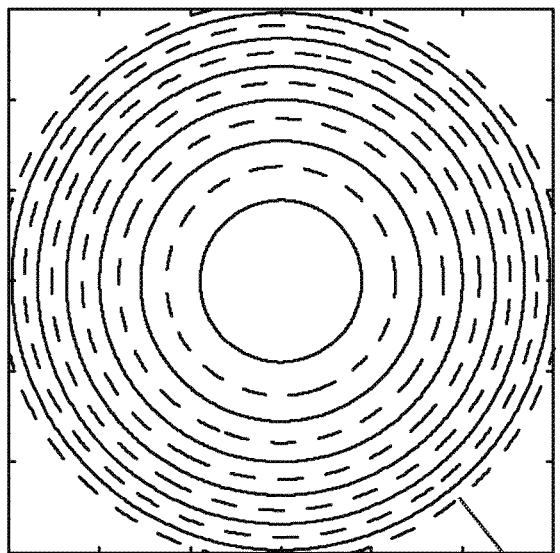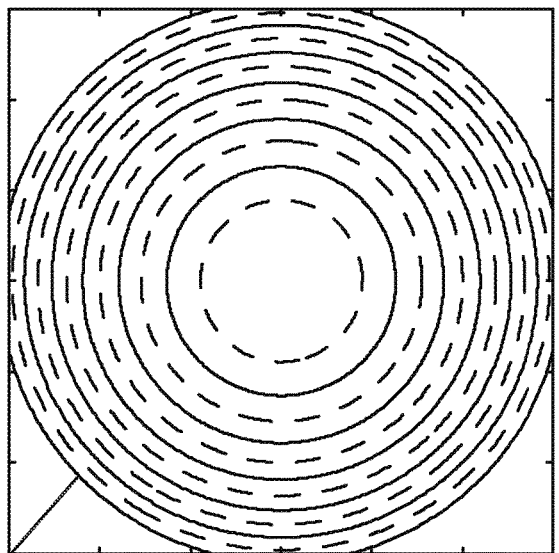
FIG. 8A  300  FIG. 8B

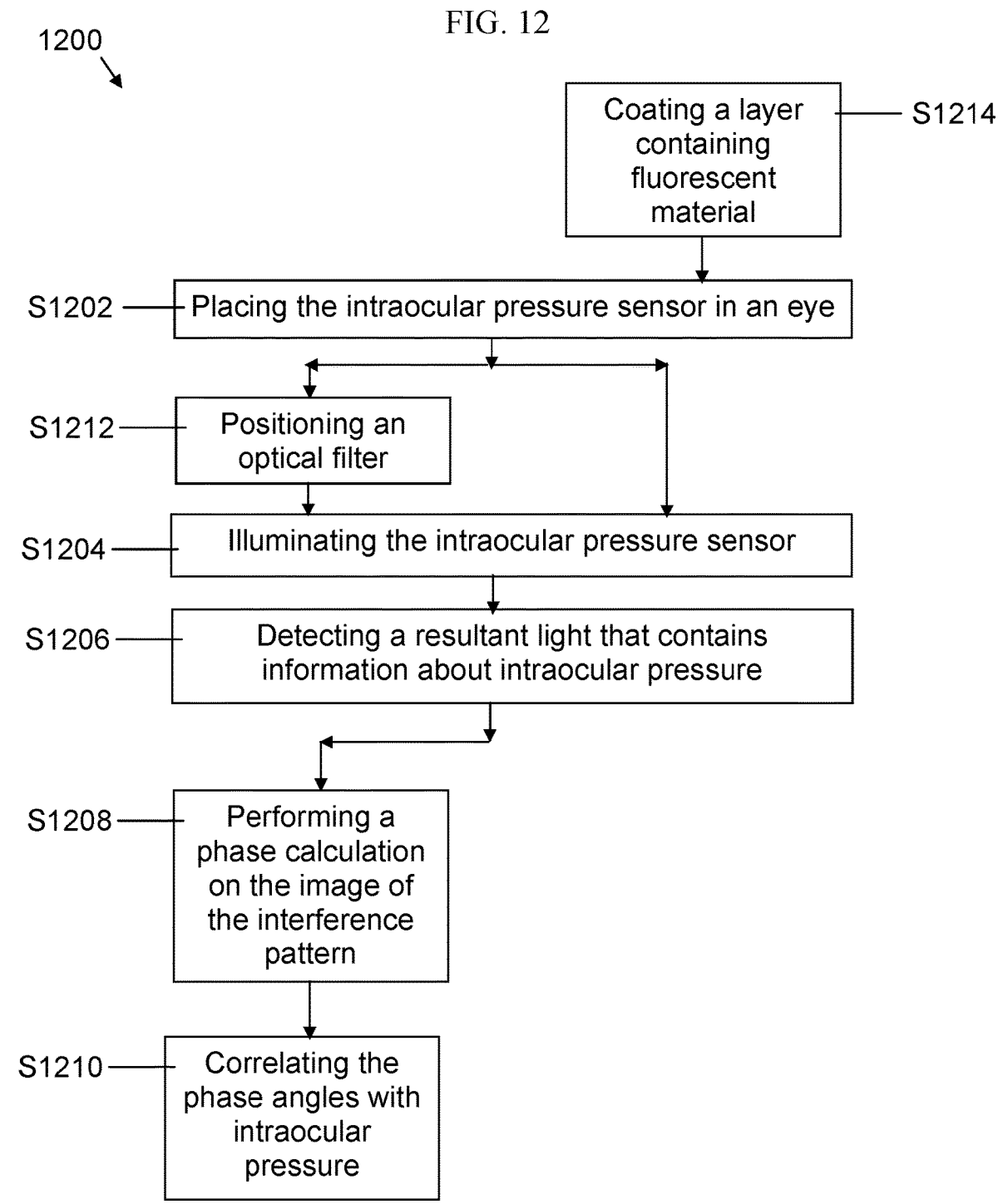

SYSTEM, DEVICE, AND METHOD FOR DETERMINATION OF INTRAOCULAR PRESSURE

CROSS-REFERENCE TO RELATED APPLICATIONS

This application is a divisional of prior application Ser. No. 12/982,110, filed Dec. 30, 2010, which claims the benefit of U.S. Provisional Patent Application No. 61/291,131, filed Dec. 30, 2009, the entire disclosures of which are hereby incorporated by reference

STATEMENT REGARDING FEDERALLY SPONSORED RESEARCH OR DEVELOPMENT

Subject matter described herein was made with U.S. Government support under contract number SBAHQ-08-I-0081 awarded by the Small Business Administration. The government has certain rights in the described subject matter.

THE NAMES OF THE PARTIES TO A JOINT RESEARCH AGREEMENT

Not applicable.

INCORPORATION-BY-REFERENCE OF MATERIAL SUBMITTED ON A COMPACT DISC

Not applicable.

BACKGROUND OF THE INVENTION

1. Field of the Invention

The present invention relates to systems, devices, and methods for measuring pressure. More particularly, the present invention relates to systems, devices, and methods for measuring intraocular pressure.

2. Background Art

Devices that measure intraocular pressure (TOP) by measuring the applanation of the cornea are known in the art. Ophthalmologists use such devices to measure IOP in a physician's office. However, these single-point measurements remain insufficient to fully manage eye disease, particularly glaucoma. TOP peaks are missed in office hours measurements, TOP fluctuations may be an independent risk factor, and a majority of glaucoma patients require changes to their topical and/or surgical management approach after multiple TOP measurements on a single day. Infrequent measurements also make it difficult to evaluate treatment effectiveness and/or to assess patient compliance. However, more frequent, longer term tonometry is labor intensive, impractical, expensive, and often conducted only upon admission to an academic hospital. Tonometers that can be used by the patient are know in the art, but these devices often cause discomfort, have proven difficult for patients to repeatably administer, and have demonstrated unacceptable error in clinical studies.

Implantable electronic devices for more frequent measurement of intraocular pressure are known in the art. Readout of passive electronic sensors has proven problematic because inductively coupling to tiny receivers in the sensor is difficult. Active sensors overcome this problem, but require implantable power sources or power storage systems, implanted integrated circuits, and large antennas. As a result, both passive and active systems have so far proven too large and complex, mostly irreversible, risky with regard to biocompatibility, and/or error prone.

BRIEF SUMMARY OF THE INVENTION

According to one aspect of the invention, a system for determination of intraocular pressure includes: an intraocular pressure sensor; a light source illuminating the intraocular pressure sensor with one or more wavelengths of light; and a detector that measures reflected and/or emitted light from the sensor. The intraocular pressure sensor includes a substrate member, a spacer member, and a flexible membrane. The substrate member, the spacer member and the flexible membrane define a sealed cavity. The flexible membrane moves and/or deforms in response to intraocular pressure changes.

In accordance with one implementation, the system further includes a processing device in communication with the detector. Then, the flexible membrane both transmits and reflects the one or more wavelengths of light, the substrate member reflects the one or more wavelengths of light transmitted by the flexible membrane, the light reflected by the substrate member interferes with light reflected from the flexible membrane to create an interference pattern, and the interference pattern corresponds to intraocular pressure. According to this implementation, the detector is an electronic imaging device capturing an image of the interference pattern, and the processing device performs a phase calculation on the image of the interference pattern to determine phase angles of the interference pattern, and correlates the phase angles with intraocular pressure.

The processing device may further perform the phase calculation using an integral transform and may calculate the phases at one or more spatial frequencies corresponding to peaks in an absolute value of the integral transform.

Also, the processing device may use the values of the spatial frequencies corresponding to peaks in the absolute value of the integral transform to correct for errors which arise from angular deviation of a sensor normal from an optical axis of a readout system.

Still further, each wavelength emitted by the light source may have a coherence length longer than the twice the separation between the flexible membrane and the substrate member.

According to this implementation, the system may further include an optical filter positioned between the intraocular pressure sensor and at least one of the light source and the electronic imaging device. The optical filter provides an optical coherence length greater than twice the distance from the flexible membrane to the substrate member.

The light source may be modulated in time to allow for lock-in detection of the interference pattern.

Further, the light source may emit multiple wavelengths of light, either simultaneously or sequentially, and the dimensions of the flexible membrane may allow a phase change in the interference pattern of greater than $2\pi$ for at least one of the multiple wavelengths of light.

In accord with another implementation, the system further includes a processing device in communication with the detector, a coating containing a fluorescent material coated on at least one of the substrate member and the flexible membrane, and a filter positioned between the intraocular pressure sensor and the detector. An external light source excites the fluorescent material of the coating, the fluorescent material of the coating emits a light of a different second wavelength, the emission of the light of the second wavelength being the result of excitation of the fluorescent material, and the proximity of the flexible membrane to the substrate member modulates the intensity of the emitted light of a different second wavelength. The detector is a light intensity sensor. The filter allows only the second wavelength to reach the detector. Then, the processing device correlates the detected intensity at the second wavelength with intraocular pressure.

According to another aspect of the invention, a device for measuring intraocular pressure includes: an intraocular pressure sensor including a substrate member, a spacer member, and a flexible membrane, the substrate member, the spacer member and the flexible membrane defining a sealed cavity wherein the flexible membrane moves and/or deforms in response to intraocular pressure changes; an anchoring member attached to the intraocular pressure sensor for immobilizing the intraocular pressure sensor in an eye; and a protective member attached to the anchoring member and covering the intraocular pressure sensor to prevent contact between the flexible membrane and portions of the eye.

In accordance with one implementation, the anchoring member comprises a plate for insertion in a scleral pocket and for immobilizing the device, and an arm for entering an anterior chamber of the eye through a scleral tunnel. The plate may include holes for suturing the plate to the eye, and/or holes for assisting wound healing.

In accordance with another implementation, the anchoring member includes a pair of pincers to enclavate an iris of the eye.

In accordance with yet another implementation, the device further includes a second intraocular pressure sensor having at least one of a different diameter, shape, membrane thickness, membrane material, and substrate material, such that the intraocular pressure sensor and the second intraocular pressure sensor provide at least one of redundant pressure measurement, failure detection, compensation for temperature fluctuations in the eye, increased pressure measurement sensitivity, and increased pressure measurement dynamic range.

The anchoring member and the protective member may be formed from a biocompatible material selected from a group consisting of polymethylmethacrylate, other acrylic plastics, silicone, other biocompatible plastics, biocompatible metals, and biocompatible metal alloys.

According to another aspect of the invention, an intraocular pressure sensor, includes: a substrate member; a spacer member; and a flexible membrane. The substrate member, the spacer member and the flexible membrane define a sealed cavity, and the flexible membrane moves and/or in response to intraocular pressure changes and the movement of the flexible membrane can be measured optically.

In accordance with one implementation, the sealed cavity has a pressure below one atmosphere.

In accordance with another implementation, light is both transmitted and reflected by the flexible membrane, and reflected by the substrate member, the light reflected by the substrate member interferes with light reflected from the flexible membrane to create an interference pattern, and the resulting interference pattern corresponds to intraocular pressure.

According to this implementation, material and dimensions of the flexible membrane may provide a number of periods in the interference pattern to estimate phase within ±0.03 radians such that intraocular pressure can be measured with an accuracy of 1 mm Hg over a range of 610 to 820 mmHg absolute pressure.

Also according to this implementation, the material and dimensions of the flexible membrane may prevent the membrane from contacting the bottom of the sealed cavity under pressures encountered in the intraocular environment.

Further in accord with this implementation, the materials and dimensions of the flexible membrane may limit pressure measurement errors to less than 1 mm Hg in the presence of temperature fluctuations from 32° C. to 36° C. typically encountered in the intraocular environment.

Still further in accord with this implementation, the material and dimensions of the flexible membrane and the thickness of the spacer member provide an interference pattern without using a light source that relies on laser action.

This implementation may further include a layer of additional material coated on the external side of the membrane, with the thickness and refractive index of the additional material equalizing the reflection from the flexible membrane and the substrate member.

Additionally, the material and dimensions of the membrane of this implementation may limit the phase change in the interference pattern to less than $2\pi$ over a range of 610 to 820 mmHg absolute pressure.

In accordance with another implementation, the intraocular pressure sensor includes a coating containing a fluorescent material, the coating being coated on at least one of the substrate member and the flexible membrane. An external light source excites the fluorescent material of the coating, and the fluorescent material of the coating emits a light of a different second wavelength, the emission of the light of the second wavelength being the result of excitation of the fluorescent material. The proximity of the flexible membrane to the substrate member modulates the intensity of the emitted light of a different second wavelength and the detected intensity of the emitted light of the different second wavelength is used to determine the pressure.

This implementation may further include a scattering medium coated on at least one of the flexible membrane and the substrate member.

Also, in accordance with this implementation, the coating may further include a second fluorescent material, and the external light source may further excite the second fluorescent material of the coating to emit a light of a different third wavelength. Then, the difference in detected intensity of the emitted light at the second and third wavelengths may be used to determine the pressure.

According to another aspect of the invention, a method for determination of intraocular pressure includes placing an intraocular pressure sensor in an eye, the intraocular pressure sensor including a substrate member, a spacer member, and a flexible membrane, the substrate member, the spacer member and the flexible membrane defining a sealed cavity wherein the flexible membrane moves and/or deforms in response to intraocular pressure changes. The method further includes illuminating, with a light source, the intraocular pressure sensor with one or more wavelengths of light, and detecting, with a detector, a resultant light that contains information about intraocular pressure.

In accordance with one implementation, the flexible membrane both transmits and reflects the one or more wavelengths of light, the substrate member reflects the one or more wavelengths of light transmitted by the flexible membrane, and the light reflected by the substrate member interferes with light reflected from the flexible membrane to create an interference pattern. The interference pattern corresponds to intraocular pressure.

According to this implementation, detecting the resultant light includes capturing, with an electronic imaging device, an image of the interference pattern, and the method further includes: performing a phase calculation on the image of the interference pattern to determine phase angles of the interference pattern; and correlating the phase angles with intraocular pressure.

Then, this implementation may further include positioning an optical filter between the intraocular pressure sensor and at least one of the light source and the electronic imaging device, the optical filter providing an optical coherence length greater than twice the distance from the flexible membrane to the substrate member.

According to this implementation, the step of illuminating the intraocular pressure sensor includes modulating the light source in time to allow for lock-in detection of the interference pattern by the electronic imaging device.

In accordance with another implementation, the method further includes coating a layer containing fluorescent material on at least one of the substrate member and the flexible membrane. Illuminating the intraocular pressure sensor includes exciting the fluorescent material of the coating with a light source such that the fluorescent material of the coating emits a light of a different second wavelength, the emission of the light of the second wavelength being the result of excitation of the fluorescent material. Then, the proximity of the flexible membrane to the substrate member modulates the intensity of the emitted light of a different second wavelength. Additionally, detecting the resultant light includes detecting an intensity of the emitted light of the different second wavelength to determine the pressure.

In accordance with another implementation, placing the intraocular pressure sensor in the eye includes immobilizing the intraocular pressure sensor in the eye using an anchoring member attached to the intraocular pressure sensor. The anchoring member may include a plate and an arm, and the immobilizing the intraocular pressure sensor in the eye may further include: inserting the plate into a scleral pocket of the eye; and inserting the arm into an anterior chamber of the eye through a scleral tunnel. Also, immobilizing the intraocular pressure sensor in the eye may include suturing the plate to the eye using holes in the plate.

According to another aspect of the invention, a method for the determination of intraocular pressure uses an interference pattern produced by an intraocular pressure sensor. The intraocular pressure sensor includes a substrate member, a spacer member, and a flexible membrane. The substrate member, the spacer member and the flexible membrane define a sealed cavity; wherein the flexible membrane moves and/or deforms in response to intraocular pressure changes. The movement or deformation of the flexible membrane is measured optically. Light from a light source, emitting one or more wavelengths of light either simultaneously or sequentially, is both transmitted and reflected by the flexible membrane, and reflected by the substrate member. The light reflected by the substrate member interferes with light reflected from the flexible membrane to create an interference pattern. The method includes: performing, by a processing device, a phase calculation on the interference pattern to determine phase angles of the interference pattern, and correlating the phase angles with pressure. The phase calculation may be performed using an integral transform and the phases may be calculated at one or more spatial frequencies corresponding to peaks in an absolute value of the integral transform. Additionally, values of the spatial frequencies corresponding to the peaks in the absolute value of the integral transform may be used to correct for errors which arise from angular deviation of a sensor normal from an optical axis of a readout system.

Other features and advantages of the invention will be set forth in, or apparent from, the detailed description of exemplary embodiments of the invention found below.

BRIEF DESCRIPTION OF THE SEVERAL VIEWS OF THE DRAWINGS

These and other features, aspects, and advantages of the present invention will become better understood with regard to the following description, appended claims, and accompanying drawings where:

FIG. 8A and FIG. 8B are representations of interference patterns having a phase change of $2\pi$;

FIG. 12 is a flow chart of an exemplary method for determination of intraocular pressure according to the invention;

DETAILED DESCRIPTION OF EXEMPLARY EMBODIMENTS OF THE INVENTION

Figure 1:
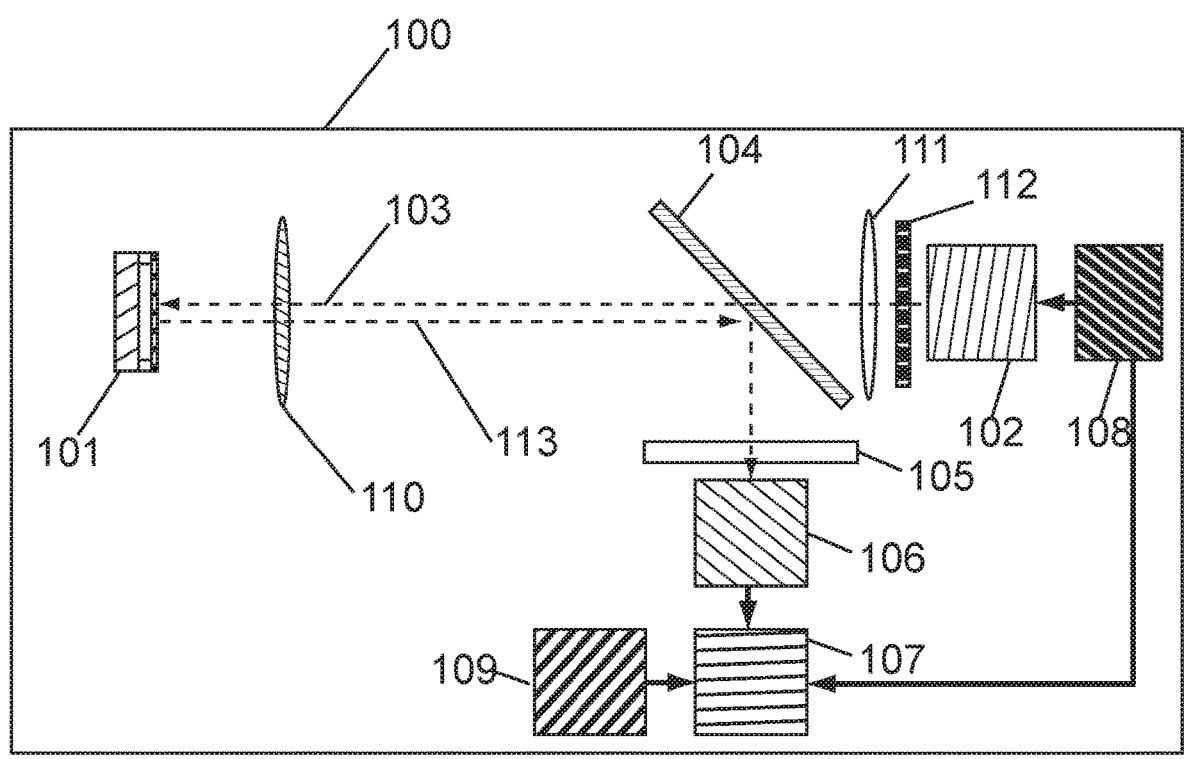
FIG. 1 is a functional block diagram of an exemplary system for determination of intraocular pressure, according to the invention.

FIG. 1 shows an exemplary system 100 for frequent measurement of intraocular pressure using an intraocular (i.e., inside or within an eye) pressure sensor 101 which, in use, would be implanted in an eye. The pressure is measured optically by the system 100 using a light source 102 to illuminate the intraocular pressure sensor 101 with one or more wavelengths of incident light 103. A resultant light 113 (comprising reflected light or a combination of reflected and emitted light) is captured by a detector 106 and the signal from the detector 106 is processed by a processing device 107 to determine the intraocular pressure.

The exemplary system 100 further comprises an objective lens 110, a beam splitter 104, an illuminating lens 111, and a diffuser 112. The objective lens 110 performs at least one of the functions of collecting light from the intraocular pressure sensor 101 and forming an image of the intraocular pressure sensor 101 on the detector 106. The beam splitter 104 allows light from the source 102 to reach the intraocular pressure sensor 101 and the reflected light from the intraocular pressure sensor 101 to reach the detector 106. The illuminating lens 111 and diffuser 112 provide well controlled, uniform illumination of the intraocular pressure sensor 101. The exemplary system 100 further comprises an atmospheric pressure sensor 109. The atmospheric pressure sensor 109 communicates with the processing device 107 to allow measurement of intraocular pressure with respect to atmospheric pressure. The atmospheric pressure sensor 109 can be an optical pressure sensor 101 as described here or one of several atmospheric pressure sensors known to those skilled in the art of pressure measurement.

Figure 2A:
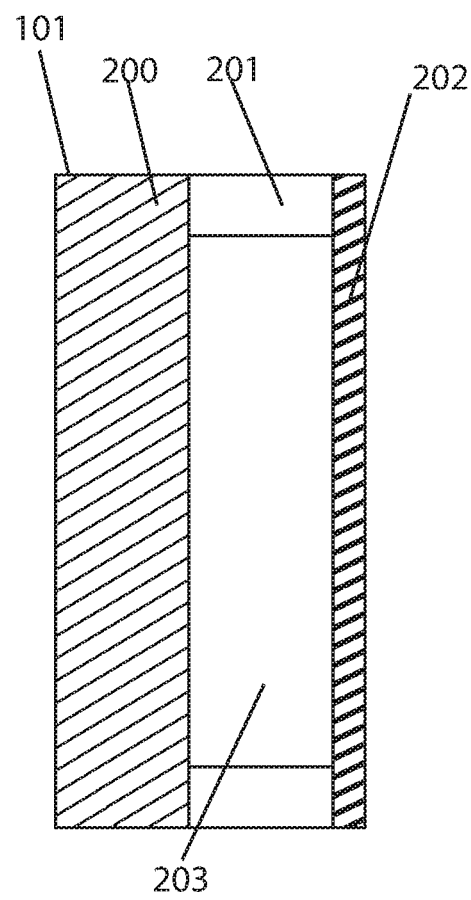
FIG. 2A and FIG. 2B are schematic cross-sectional views of exemplary intraocular pressure sensors according to the invention.
Figure 3A:
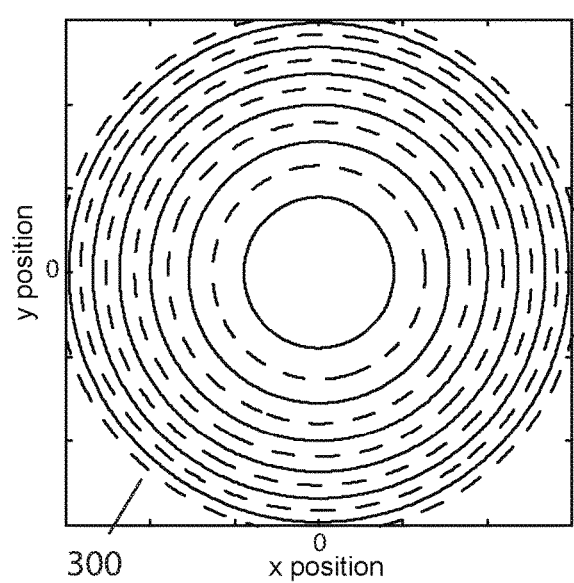
FIG. 3A is a representation of an image of an exemplary interference pattern.

FIG. 2A shows an exemplary intraocular pressure sensor 101 comprising a substrate member 200, a spacer member 201, and a flexible membrane 202 which define a sealed cavity 203. The flexible membrane 202 deflects in response to changes in intraocular pressure and these changes can be measured optically. The incident light 103 is both transmitted and reflected by the flexible membrane 202, and reflected by the substrate member 200. The light reflected by the substrate member 200 interferes either constructively or destructively with light reflected from the flexible membrane 202 such that the resultant light 113 (FIG. 1) comprises an interference pattern 300, as shown in FIG. 3A.

The interference pattern 300 consists of bright and dark regions that are referred to as interference fringes. The brightest and darkest levels of the interference pattern 300 are shown as solid and dashed contour lines in FIG. 3A. These interference fringes change position when the flexible membrane 202 deflects in response to intraocular pressure changes as described in more detail below. Thus, the interference pattern 300 corresponds to intraocular pressure.

The interference pattern 300 is captured using the detector 106 (FIG. 1). In an embodiment the detector 106 is an electronic imaging device such as a digital camera or photodetector array. In an embodiment, the detector 106 communicates with a processing device 107 which performs a phase calculation on the image of the interference pattern 300 and correlates the calculated phase angles with intraocular pressure.

Figure 3B:
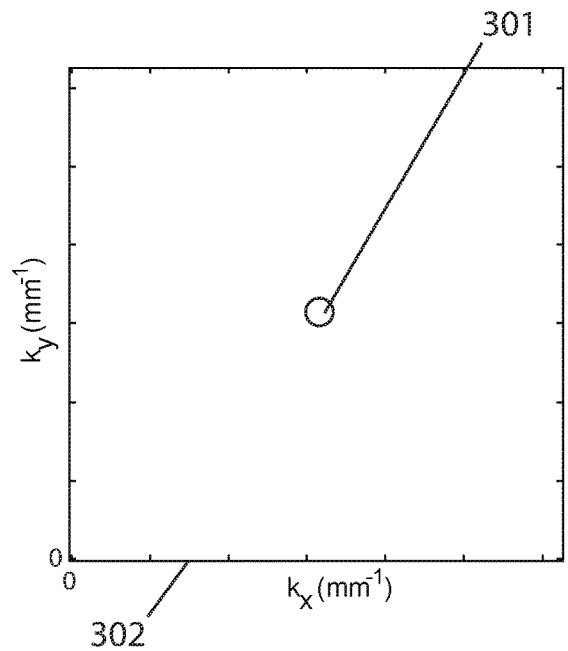
FIG. 3B is a graph of an absolute value of an integral transform of the exemplary interference pattern of FIG. 3A.
Figure 3C:
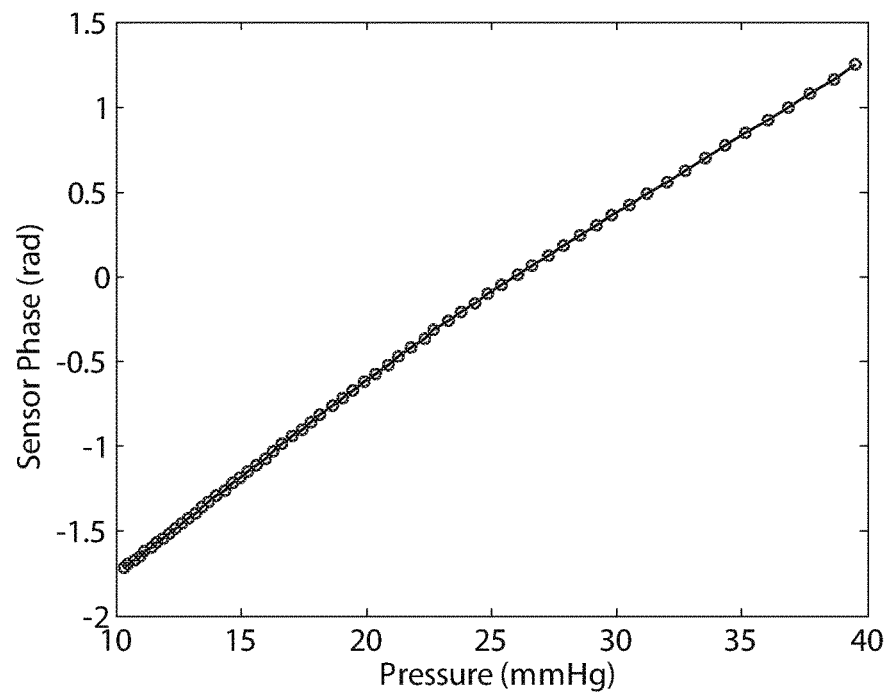
FIG. 3C is a graph of an experimentally measured relationship between phase of an interference pattern and liquid pressure for an exemplary intraocular pressure sensor.

FIG. 3C shows the experimentally measured relationship between the phase of the interference pattern 300 and liquid pressure for an intraocular pressure sensor 101 with a silicon substrate member 200, a silicon nitride flexible membrane 202, illuminated with a light emitting diode light source 102 at a wavelength of similar to 800 nm.

As shown in FIG. 3B, the processing device 107 (FIG. 1) performs the phase calculation using an integral transform and calculates the phase at one or more spatial frequencies corresponding to peaks 301 in an absolute value of the integral transform 302. This calculation further allows for correction of pressure readings for angular deviations between the optical axes of the detector 106 and the intraocular pressure sensor 101, as described in more detail below.

Figure 4A:
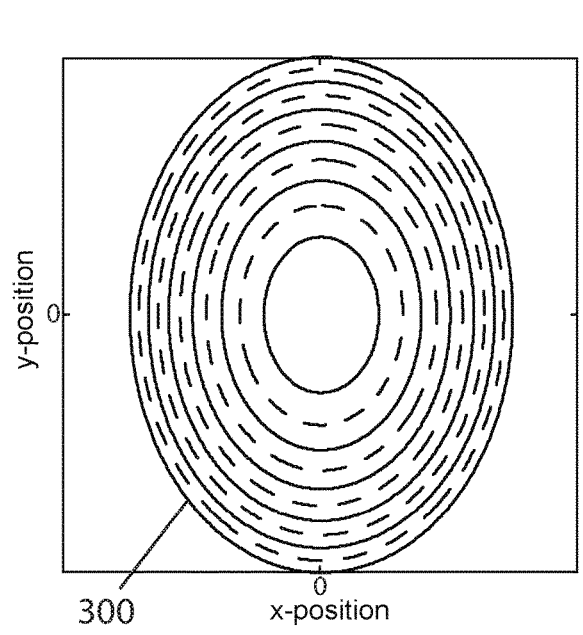
FIG. 4A is another representation of an image of an exemplary interference pattern.

FIG. 4A shows an interference pattern 300 from a sensor 101 whose optical axis is tilted about the y-axis effectively compressing the pattern along the x-direction.

Figure 4B:
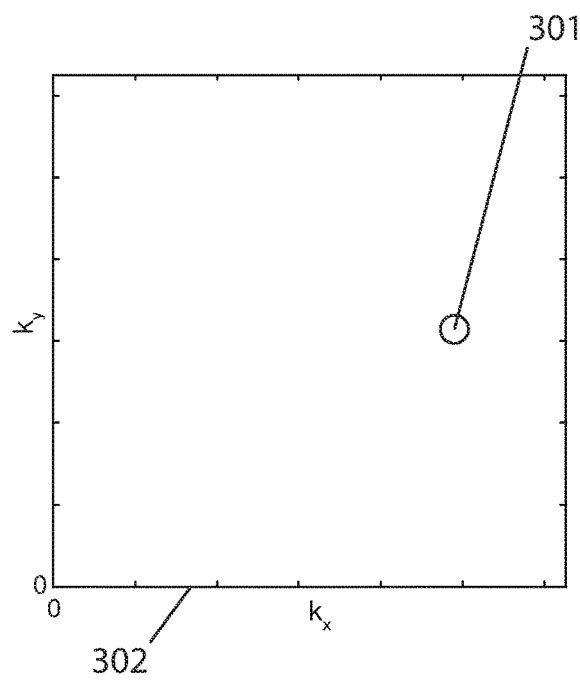
FIG. 4B is a graph of an absolute value of an integral transform of the exemplary interference pattern of FIG. 3A.

FIG. 4B, discussed below, shows the absolute value of an integral transform 302 of the interference pattern 300.

Figure 2B:
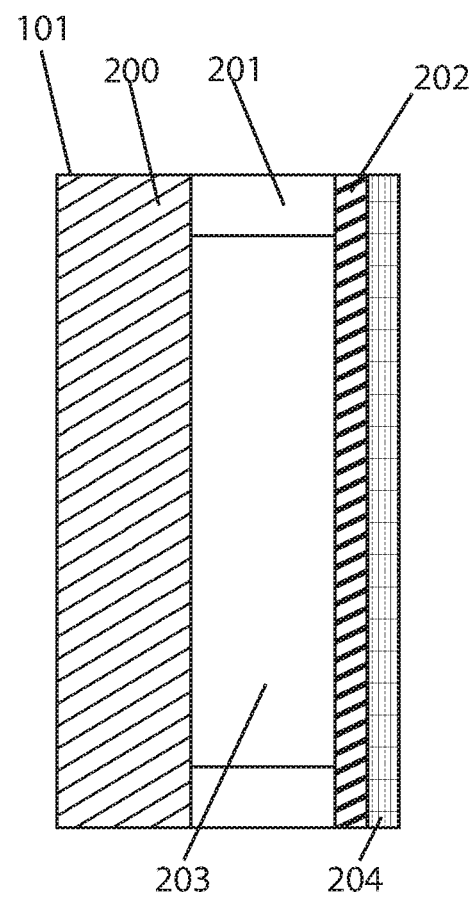

In an embodiment each wavelength emitted by the light source 102 (FIG. 1) has a coherence length longer than twice the separation between the flexible membrane 202 and the substrate member 200 (FIGS. 2A and 2B). Having a sufficiently long coherence length ensures that the interference pattern 300 (FIG. 3A) can be clearly captured by the detector 106 (FIG. 1). A shorter coherence length could be contemplated, but would reduce the visibility of the interference pattern 300 and thus reduce the signal to noise ratio of the detector 106 signal.

In an embodiment the light source 102 is a light emitting diode. A light emitting diode is preferred because it emits a narrow range of wavelengths such that the coherence length of the incident light 103 and resultant light 113 is between 1 μm and 1000 μm. This is appropriate for the range of sealed cavity 203 thicknesses described in more detail below. Laser light sources also offer sufficiently long coherence lengths, but light emitting diodes offer greater eye safety.

In the exemplary system 100 shown in FIG. 1, an optical filter 105 is positioned between the intraocular pressure sensor 101 and at least one of the light source 102 and the detector 106. The optical filter 105 increases the coherence length of at least one of the incident light 103 and resultant light 113. The optical filter 105 is required if the light source 102 does not have an intrinsically long enough coherence length. In a preferred embodiment the filter is positioned immediately in front of the detector so as to block other light not at the wavelength of the resultant light 113.

In a preferred embodiment the wavelengths of the incident light 103 are in the infrared spectral region so that the incident light 103 remains invisible to the patient.

In an embodiment, the light source 102 is modulated in time by a modulator 108 which also communicates with the processing device 107. The modulator modulates the light source by at least one of electrical or mechanical means or some combination of electrical and mechanical means. The modulator 108 has a frequency such that many cycles are contained in a single intraocular pressure measurement. The modulating signal can be any of several periodic signals, such as a sine wave or square wave, that are familiar to those skilled in the art. The signal from the modulator 108 is also routed to the processing device 107 where it is combined with the signal from the detector 106 for phase-locked (or "lock-in") detection, a technique well known to those skilled in the art of low-level signal measurements. This detection method reduces noise that could be introduced by light sources, for example room lights, other than the resultant light 113.

In an embodiment the light source 102 emits multiple wavelengths of light in order to improve at least one of the precision and dynamic range of the pressure measurement. This is particularly important for designs of the intraocular pressure sensor 101 in which the deflection of the flexible membrane 202 yields a phase change of greater than $2\pi$.

FIG. 8A and FIG. 8B show interference patterns 300 having a phase change of $2\pi$.

A single wavelength measurement of a single intraocular pressure sensor 101 (FIG. 1) would exhibit pressure ambiguities if the phase changes by more than $2\pi$, as described in more detail below.

Figure 9A:
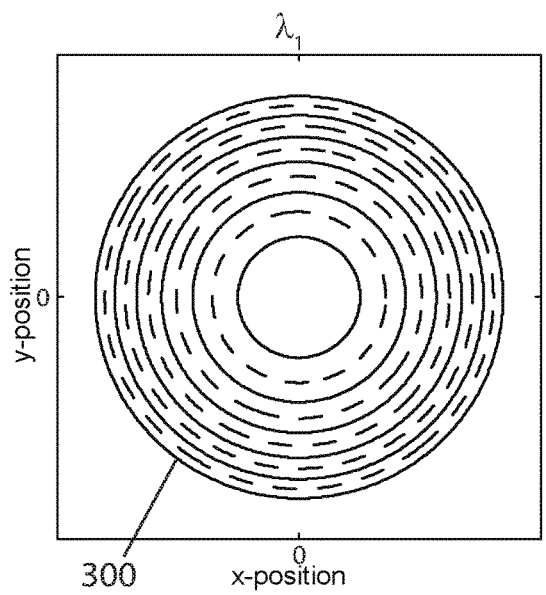
FIG. 9A and FIG. 9B are representations of interference patterns associated with multiple, sequentially emitted wavelengths.
Figure 9B:
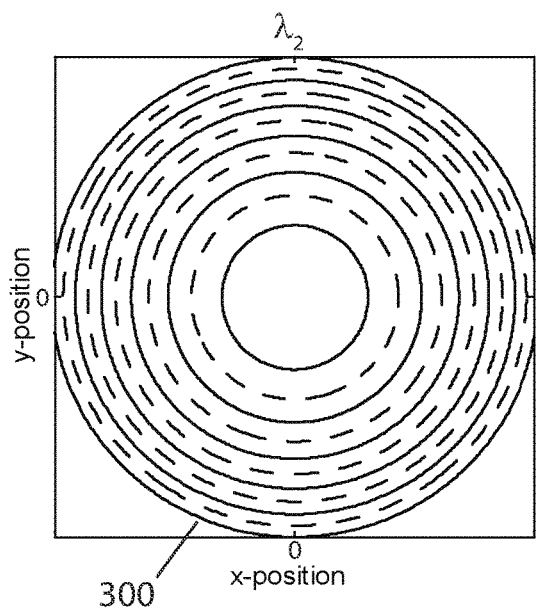

FIG. 9A and FIG. 9B show interference patterns 300 associated with each wavelength captured by the detector 106 in an embodiment where multiple wavelengths are emitted sequentially. The processing device 107 (FIG. 1) calculates the phase angle of each interference pattern 300 at spatial frequencies corresponding to the illuminating wavelengths as described in more detail below.

Figure 10A:
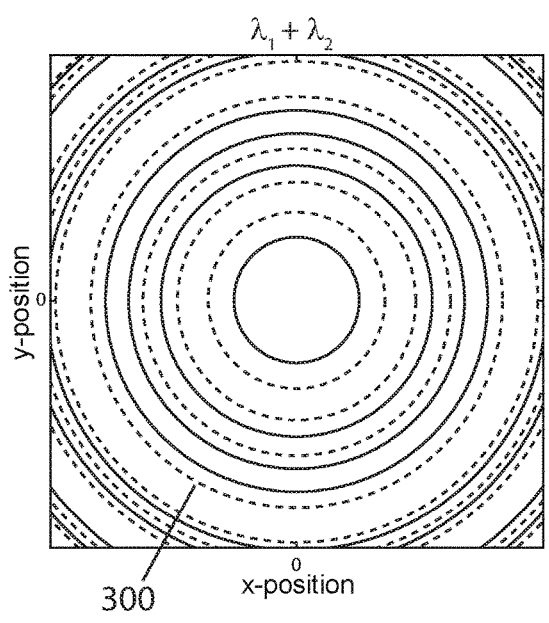
FIG. 10A is a representation of an interference pattern associated with multiple, simultaneously emitted wavelengths.

As shown in FIG. 10A, in an alternative embodiment the light source 102 emits the multiple wavelengths simultaneously, and a more complex interference pattern 300 is generated. The processing device 107 now calculate the phase angles from a single interference pattern 300 but at multiple spatial frequencies, each spatial frequency corresponding to a different wavelength, as described in more detail below.

Figure 7A:
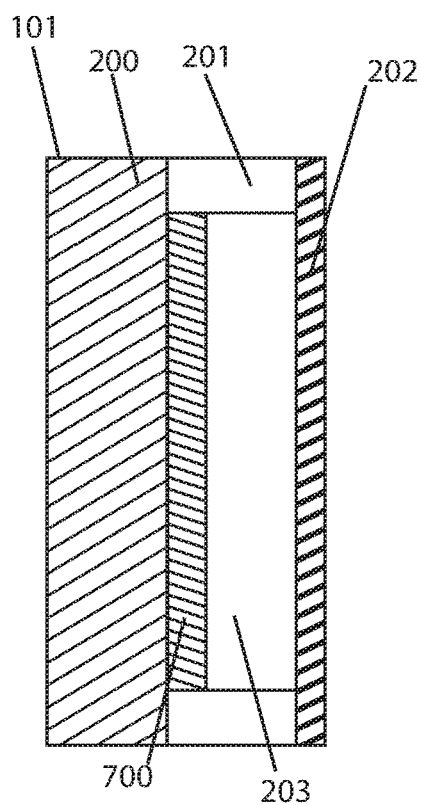
FIG. 7A through FIG. 7D are schematic cross-sectional views of exemplary intraocular pressure sensors according to the invention further comprising a coating containing a fluorescent material.
Figure 7B:
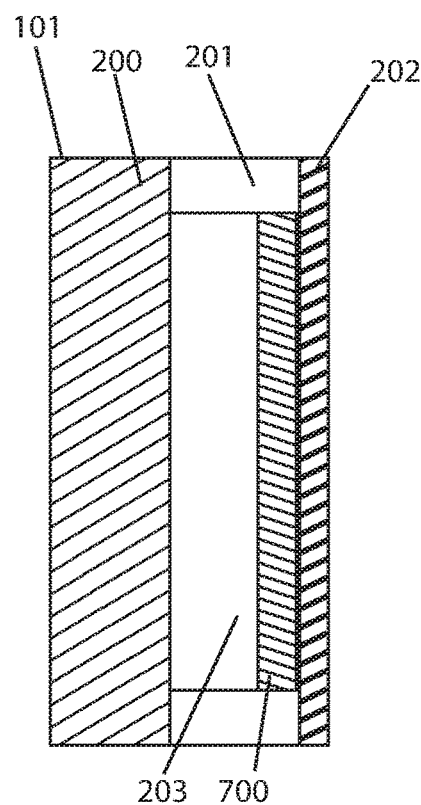

In yet another embodiment, as shown in FIG. 7A and FIG. 7B respectively, the intraocular pressure sensor 101 further comprises a coating 700 containing a fluorescent material, the coating 700 being coated on at least one of the substrate member 200 and the flexible membrane 202. As used herein, a fluorescent material is a material which absorbs electromagnetic energy of a specific first wavelength and re-emits energy at different (but equally specific) additional wavelengths. A fluorophor is a component, such as a fluorescent dye molecule, of a fluorescent material which absorbs electromagnetic energy of a specific first wavelength and re-emits energy at different (but equally specific) second wavelength. A fluorescent material may contain one or more fluorophors. The incident light 103 excites the fluorescent material of the coating 700, and the fluorescent material of the coating 700 emits light of a different second wavelength, the emission of the light of the second wavelength being the result of excitation of the fluorescent material. After passing back through the flexible membrane, and perhaps being further modulated, the emitted light of a different second wavelength becomes the resultant light 113.

In an embodiment, the proximity of the flexible membrane 202 to the substrate member 200 modulates the intensity of the resultant light 113. In an embodiment the intensity of the resultant light 113 from the intraocular pressure sensor 101 is modulated based on several phenomena described in more detail below. In an embodiment the detector 106 is one or more light intensity sensors. The light intensity sensors may be at least one of photodiodes or photomultipler tubes. The signal from the detector 106 corresponds to intraocular pressure, and the processing device 107 processes the signal to determine intraocular pressure. In an embodiment the optical filter 105 is placed between the intraocular pressure sensor 101 and the detector 106 such that only the second wavelength in the resultant light 113 reaches the detector 106.

Movement of the intraocular pressure sensor 101 with respect to the assembly containing the detector 106 must be considered. The assembly may be at least one of a handheld unit, a head mounted unit, and an eye glass mounted unit. The assembly may or may not contain the light source 102.

In an embodiment relative motion is limited by providing a target at which the patient gazes while the pressure measurement is acquired. The target can be real structure or a virtual image created using optics within the assembly. Those skilled in the art have found that angular motions are limited to less than 0.2 degrees during visual fixation.

In an embodiment an eye cup can be added to the assembly containing the detector 106. The eye cup contacts the face during the pressure measurement in order to physically limit movement of the intraocular pressure sensor 101 with respect to the detector 106.

In an embodiment, at least one of autofocus mechanisms or image stabilization mechanisms, familiar to those skilled in the art, are added to the assembly to minimize the movement of the sensor 101 image and the detector 106.

In an embodiment the detector 106 is an electronic image sensor with a frame rate in excess of 100 frames per second. The frame rate allows images to be captured during times when the sensor is in focus and within the field of view of the electronic image sensor.

The processing device 107 is preferably at least one of a dedicated electronic circuit, a microprocessor, a digital signal processor, or a programmable logic device. The processing device 107 may be either internal or external to the assembly containing the detector 106. The processing device is connected to the detector by at least one of a physical electrical connection, a wireless connection, or a network connection all of which are familiar to those skilled in the art.

Figure 5A:
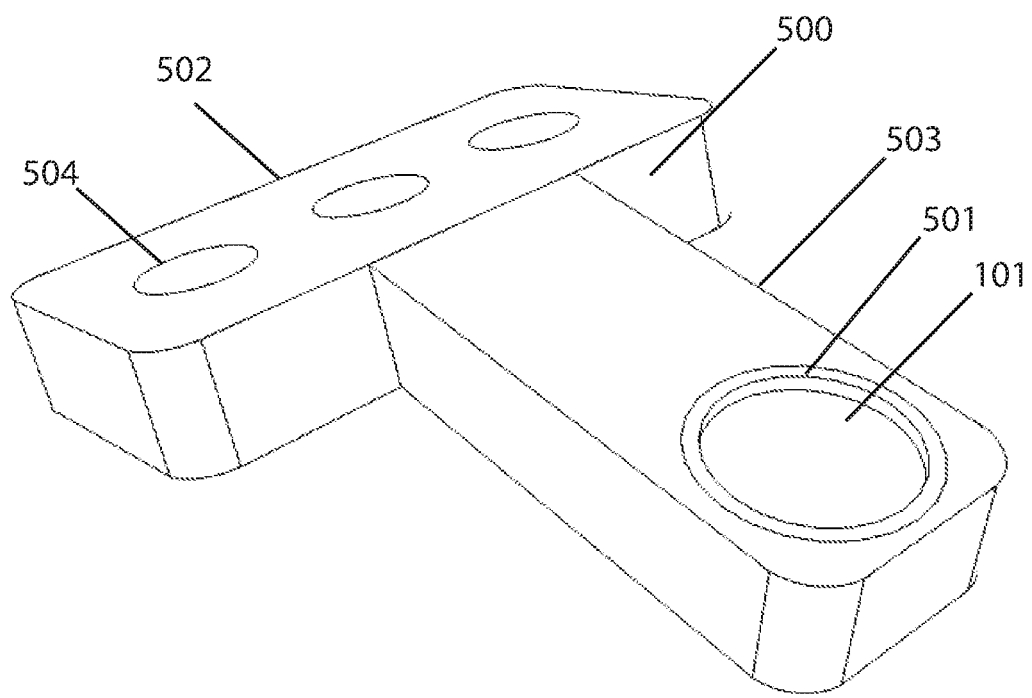
FIG. 5A is a schematic perspective view of an exemplary embodiment of a device for measuring intraocular pressure according to the invention.

FIG. 5A shows a device for measuring intraocular pressure comprising an intraocular pressure sensor 101 and an anchoring member 500. The anchoring member comprises a protective member 501, a plate 502, and an arm 503.

Figure 5B:
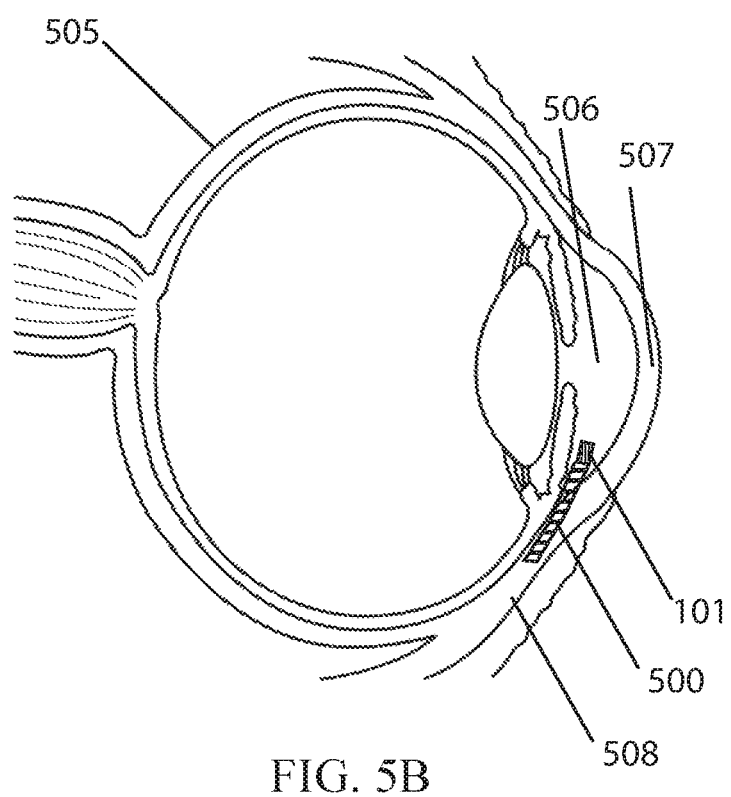
FIG. 5B is a schematic sectional view of an eye with the device of FIG. 5A implanted therein.

FIG. 5B shows an eye 505 with the device implanted through the sclera 508 such that the intraocular pressure sensor 101 is located in the anterior chamber 506 and is visible through the cornea 507. The protective member 501 prevents the intraocular pressure sensor 101 from contacting the cornea 507 in case of movement of the sensor toward the cornea 507. The dimensions of the plate 502 are chosen so that it can be fixed in a scleral pocket. Although other dimensions could be contemplated, a long dimension of 1 to 5 mm and a short dimension of 1 to 3 mm are appropriate.

In one embodiment the plate 502 contains holes 504 for suturing the anchoring member 500 to the sclera 508. Although other dimensions could be contemplated, the diameter of the holes should be greater than approximately 50 µm to permit an atraumatic needle and suture to pass.

In an embodiment the plate 502 contains holes 504 to assist in wound healing. In this case the sclera 508 closes through the holes to promote both healing and immobilization of the device. The dimensions of the arm 503 are such that the arm can extend through a scleral tunnel placing the intraocular pressure sensor 101 in a position within the anterior chamber 506 such that the intraocular pressure sensor 101 is visible through the cornea 507. Other dimensions could be contemplated, but an arm width of 1 to 2 mm and an arm length of 2 to 7 mm are acceptable.

Figure 6A:
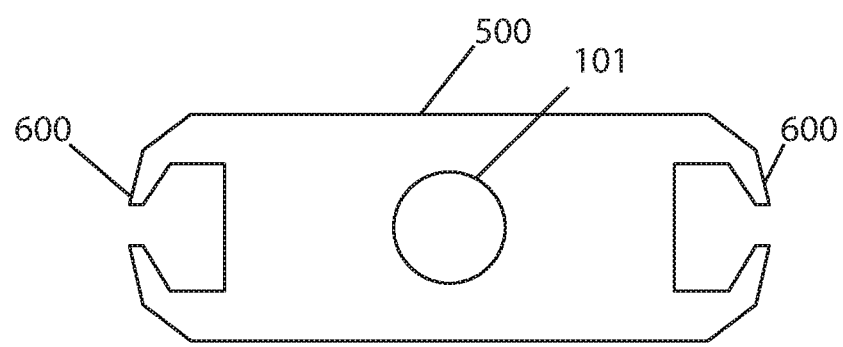
FIG. 6A is a schematic plan view of another exemplary embodiment of a device for measuring intraocular pressure according to the invention.
Figure 6B:
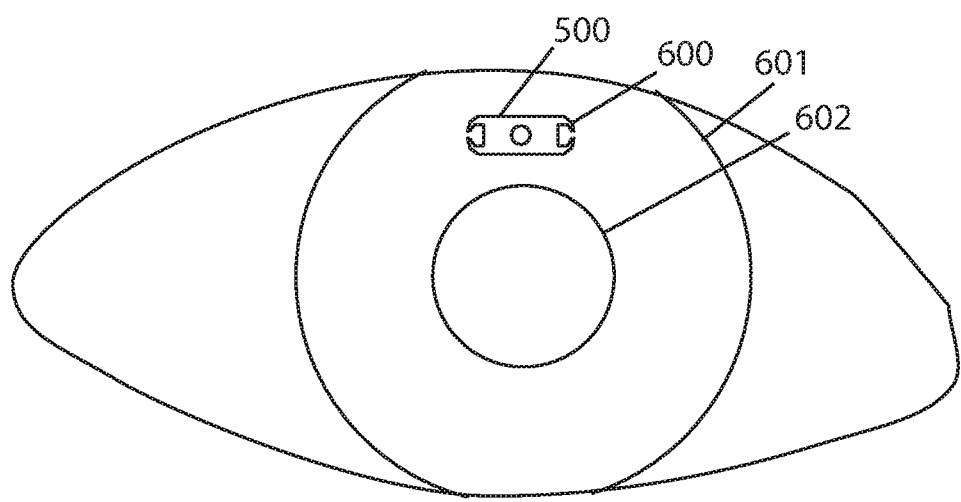
FIG. 6B is a schematic plan view of an eye with the device of FIG. 6A implanted therein.

In an embodiment shown in FIG. 6A and FIG. 6B, the anchor member 500 comprises a pair of 600 on at least one end such that it can be attached to the iris 601 rather than fixed in the sclera 508. In this embodiment the anchor member 500 along with the attached intraocular pressure sensor 101 is inserted into the anterior chamber 506 and placed on the iris 601 such that it does not block the pupil 602. The tissue of the iris is enclavated by the pincers 600 to immobilize the anchor member 500 in the eye 505.

Figure 14A:
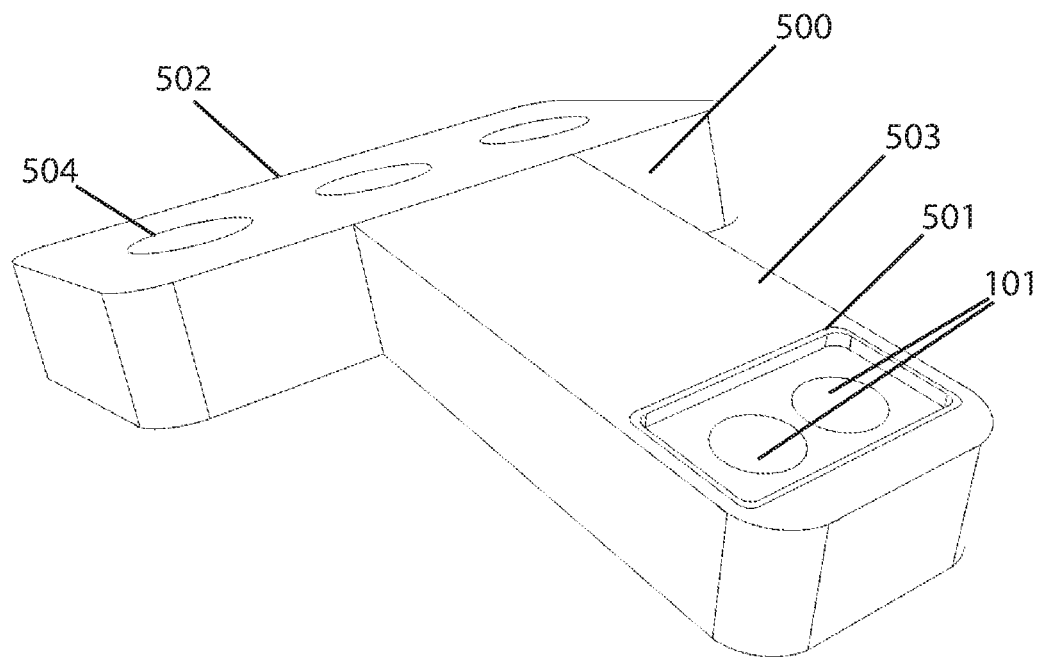
FIG. 14A and FIG. 14B are schematic perspectives view of further exemplary embodiments of a device for measuring intraocular pressure according to the invention.

In an embodiment shown in FIG. 14A two or more intraocular pressure sensors 101 can be included in the same device. This provides redundant pressure measurements that increase confidence in the pressure reported by the intraocular pressure measurement system 100. In addition, if one sensor fails, the deviation in readings between the first sensor and any additional sensors will serve as an indication of the failure.

Figure 14B:
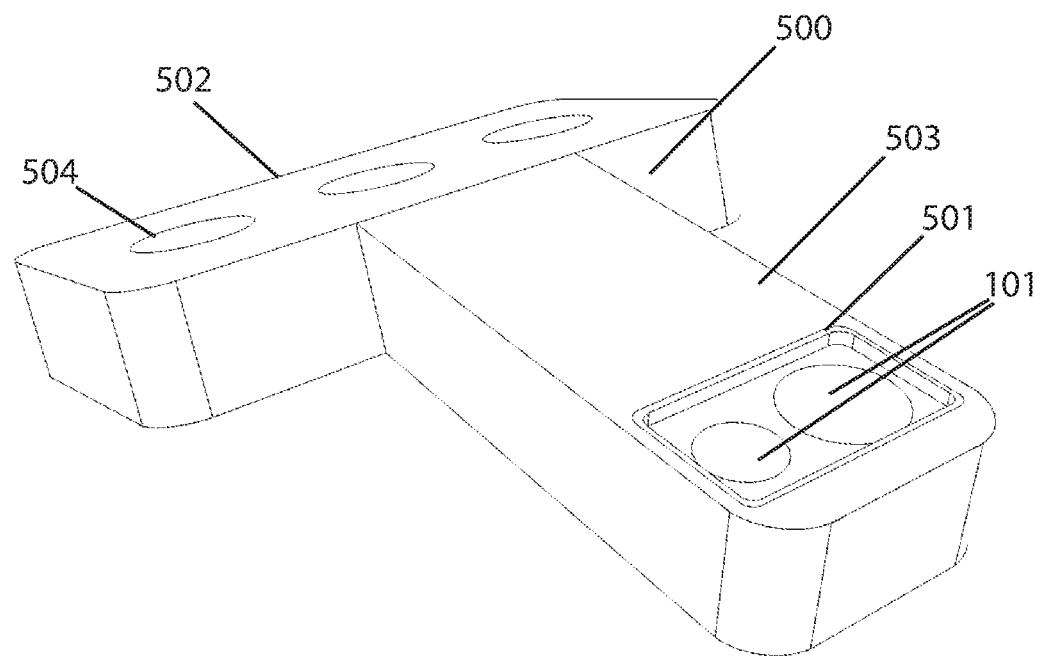

In an embodiment shown in FIG. 14B, the second intraocular pressure sensor 101 has at least one of a different diameter, shape, flexible membrane 202 thickness, flexible membrane 202 material, and substrate member 200 material. The two or more pressure sensors 101 provide at least one of redundant pressure measurement, failure detection, compensation for temperature fluctuations in the eye, increased pressure measurement precision, increased pressure measurement dynamic range. In this embodiment, the flexible membrane 202 deflection due to temperature changes and the flexible membrane 202 deflection due to pressure changes are different for the two different sensors 101. Thus, the pressure and temperature can be separately measured by solving a set of simultaneous equations of the form:

$$(\theta_1 - \theta_{01}) = S_{1T}(T - T_0) + S_{1P}(P - P_0)$$

$$(\theta_2 - \theta_{02}) = S_{2T}(T - T_0) + S_{2P}(P - P_0)'$$

where $\theta_1$ and $\theta_2$ are the phases for the interference pattern 300 or the intensities associated with the fluorescence for the first and second sensor respectively. $\theta_{01}$ and $\theta_{02}$ are known reference phases for the interference pattern 300 or known reference intensities associated with the fluorescence for the first and second sensor respectively. $S_{1T}$ and $S_{2T}$ are the sensitivities of the first and second sensor to changes in temperature, for example in radians/° C. or intensity/° C., $S_{1P}$ and $S_{2P}$ are the sensitivities of the first and second sensor to changes in pressure, for example in radians/mmHg or intensity/mmHg, T is the temperature and $T_0$ is a known reference temperature, and P is the pressure and $P_0$ is a known reference pressure.

An exemplary device with two intraocular pressure sensors 101 includes one sensor with diameter similar to 300 um and another with diameter similar to 400 um. The flexible membrane 202 thickness is similar to 1.5 μm for both sensors. The sensitivities of the two intraocular pressure sensors 101 to changes in pressure are similar to 0.020 radians/mmHg and 0.037 radians/mmHg respectively for intraocular pressure ranges from 730 mmHg to 780 mmHg (10 to 50 mmHg above atmospheric pressure at sea level). The sensitivity of the two sensors 101 to changes in temperature are similar to 0.014 radians/° C. and 0.023 radians/° C. respectively. Thus, the interference patterns 300 from the two sensors allow differentiation between changes in pressure and temperature.

In an embodiment, the flexible membrane 202 deflection due to pressure changes is different for two sensors 101. Pressure is determined by measuring the phase angles of the interference patterns 300 from both sensors. If the phase change for at least one of the interference patterns 300 exceeds 2π the pressure can still be determined uniquely based on the phase of the other interference pattern. In addition, if the desired dynamic range is kept constant, the use of two sensors with higher sensitivity, but at least one with total phase change greater than 2π, can improve sensitivity and thus sensing precision and accuracy.

An exemplary device with two intraocular pressure sensors 101 includes one sensor 101 with diameter similar to 300 um and flexible membrane thickness similar to 1.5 μm and another sensor 101 with flexible membrane 202 diameter similar to 600 um and flexible membrane 202 thickness similar to 200 nm. The sensitivity of the two sensors 101 to changes in pressure are 0.020 radians/mmHg and 0.074 radians/mmHg respectively from 730 mmHg to 780 mmHg. For a desired dynamic range of 610 to 820 mmHg the first sensor undergoes a total phase change of similar to 4.8 radians and the second sensor undergoes a total phase change similar to 16 radians. In this exemplary case the first sensor 101 provides a coarse measurement of pressure with no ambiguity over the entire pressure range, and the second sensor 101 provides a more sensitive measurement of pressure with ambiguity among several pressures within the range. However, the first sensor 101 removes this ambiguity. Using two sensors 101 allows intraocular pressure to be measured with greater sensitivity without sacrificing dynamic range. Other sensor designs can be contemplated that would expand dynamic range without sacrificing sensitivity.

The anchoring member 500 is formed from materials that are biocompatible when implanted in the eye. Possible materials include polymethylmethacrylate, other acrylic plastics, and silicone. These materials are commonly used for intralocular lenses. In addition, biocompatible metals and metal alloys containing elements such as gold or titanium are possible materials for the anchoring member.

As discussed above, FIG. 2A shows an intraocular pressure sensor 101 comprising a substrate member 200, a spacer member 201, a flexible membrane 202 which define a sealed cavity 203. The flexible membrane 202 deflects in response in response to intraocular pressure changes and the deflection of the flexible membrane 202 can be measured optically. The substrate member 200 consists of at least one biocompatible metal, semiconductor, or insulator material. The spacer member 201 consists of at least one biocompatible metal, semiconductor, or insulator material. The spacer member 201 prevents fluid from penetrating into the sealed cavity 203. In an embodiment the spacer member 200 material is at least one of silicon, silicon nitride, and silicon dioxide. The spacer member 201 can be formed by one of several processes familiar to those skilled in the art of microfabrication including at least one of etching or deposition.

In a preferred embodiment the sealed cavity 203 has a pressure below one atmosphere. The reduced cavity pressure reduces the temperature sensitivity of the device because expansion or contraction of the gas inside the cavity will not create large changes in the separation of the flexible membrane 202 from the substrate member 200. A sealed cavity 203 with reduced pressure can be formed by one of several processes familiar to those skilled in the art of microfabrication including at least one of vacuum contact bonding, vacuum anodic bonding, vacuum adhesive bonding, thermal annealing, etching through release holes and low pressure chemical vapor deposition sealing of these holes, and gettering of residual gas in the cavity.

The flexible membrane 202 is substantially impermeable to gas or liquid in order to maintain the integrity of the sealed cavity 203 over the life of the intraocular pressure sensor 101. In a preferred embodiment, the flexible membrane 202 consists of silicon nitride. Silicon nitride is one of the best known moisture and gas barriers, with no measurable permeation, even at 1100° C.

In an embodiment, an incident light 103 (FIG. 1) strikes the intraocular pressure sensor 101 and is partially reflected and partially transmitted by the flexible membrane 202. The transmitted light is partially reflected by the substrate member 200. Reflected light from the flexible membrane 202 and the substrate member 200 combine to form a resultant light 113. Light reflected by the substrate member 200 interferes either constructively or destructively with light reflected from the flexible membrane 202 to create an interference pattern 300 (FIG. 3). The resulting interference pattern 300 corresponds to intraocular pressure, as described in more detail below.

The substrate member 200 consists of a material with the correct optical properties and surface finish to at least partially reflect light at the illumination wavelength. The substrate member 200 material is chosen from a group including at least one of biocompatible metals, semiconductors, or insulators. In an embodiment, the substrate member 200 is made of polished silicon which is partially reflective throughout the visible and near-infrared spectral region. In another embodiment the substrate member 200 is made from a glass, plastic, semiconductor, or oxide material. In another embodiment, the substrate member 200 material is optically transparent for visible wavelengths but is reflective at infrared wavelengths. In another embodiment, the substrate member 200 is coated with another layer of material or multiple layers of materials to render it reflective in the infrared. In this way the sensor is transparent in the visible spectral region but reflective in the infrared region to improve the aesthetics of the sensor.

The flexible membrane 202 consists of a material with the correct optical properties and correct thickness to partially, but not entirely, reflect an incident light 103. In this way an optical cavity is formed and an optical interference pattern 300 is generated. In one embodiment a flexible membrane 202 consists of at least one of silicon, silicon nitride, and silicon dioxide. A flexible membrane 202 can be formed by one of several processes familiar to those skilled in the art of microfabrication including at least one of implantation, oxidation, physical vapor deposition, chemical vapor deposition, and etching.

The interference pattern 300 consists of bright and dark regions that are often referred to as interference fringes. These interference fringes change position when the flexible membrane 202 deflects with respect to the substrate member. The separation of these rings depends on the curvature of the flexible membrane 202 surface. If the separation of the flexible membrane 202 and the substrate member 200 changes then the rings shift in radial position. If the curvature of the flexible membrane 202 surface changes then the spacing of the rings changes. The visibility, the difference in intensity between brightest and darkest points divided by sum of the intensities between the brightest and darkest points, of the rings at the detector 106 is determined by the separation of the substrate member 200 and the flexible membrane 202 and the coherence length of the resultant light 113.

The materials and dimensions of the flexible membrane allow a number of periods in the interference pattern 300 and sufficient deflection to detect clinically important changes in intraocular pressure. In it known that intraocular pressure changes of 1 mmHg have clinical significance in managing glaucoma. In an exemplary sensor the flexible membrane 202 is circular with a diameter of 300 µm and a thickness of 1.5 The sealed cavity 203 contains a vacuum. The spacer member is greater than 5 µm thick but less than twice the coherence length of the incident light 103. At 820 mmHg absolute pressure (60 mmHg above atmospheric pressure at sea level) the flexible membrane 202 deflects similar to 3.6 µm at its central point. This gives rise to 9 periods in the interference pattern 300 when illuminated with an incident light 103 of 800 nm wavelength. To measure intraocular pressure from 10 to 60 mmHg with respect to atmospheric pressure at elevations from sea level to 2000 m the sensor 101 measures absolute pressures from 610 mmHg to 820 mmHg. For a light source 102 emitting a single wavelength, the interference pattern 300 is limited to a maximum phase change of 2n over this pressure range. Thus the intraocular pressure measurement system 100 must measure the phase to ±0.03 radians to maintain an accuracy of 1 mmHg. With a signal to noise ratio as low as 1, the standard deviation of the phase estimate is similar to 0.01 radians when the signal is captured using only 200×200 pixel electronic image sensor. We define signal to noise ratio as the square of the amplitude of the interference pattern 300 modulation divided by the variance of an additive Gaussian noise. This noise level is much larger and the image resolution much smaller than what would be typically encountered in practice, thus the precision of the phase measurement is sufficient to detect clinically relevant changes in intraocular pressure.

The material and dimensions of the flexible membrane 202 and the dimensions of the spacer layer 201 prevent the membrane 202 from contacting the bottom of the sealed cavity 203 under pressures encountered in the intraocular environment. In an exemplary sensor 101 the flexible membrane 202 consists of non-stoichiometric, low-stress silicon nitride with an elastic modulus similar to 200 GPa and a Poisson ratio similar to 0.27. The flexible membrane 202 diameter is 300 µm and the flexible membrane 202 thickness is 1.5 The sealed cavity 203 contains a vacuum. At 820 mmHg absolute pressure (60 mmHg above atmospheric pressure at sea level) the flexible membrane 202 deflects similar to 3.6 µm toward the substrate member 200 at its center. If the spacer member 201 is greater than 3.6 µm thick then the flexible membrane 202 will not contact the substrate member 200. Other dimensions and materials could be contemplated that also prevent contact between the flexible membrane 202 and the substrate member 200.

In a preferred embodiment an intraocular pressure sensor 101 limits pressure measurement errors to 1 mmHg in the presence of temperature fluctuations from 32° to 36°. This range represents the approximate range of corneal temperature variation for ambient temperatures ranging from 18° C. to 27° C. It is known that variations in corneal temperature represent an upper bound on variations in the anterior chamber. In an exemplary sensor 101 the flexible membrane 202 consists of non-stoichiometric, low-stress silicon nitride with an elastic modulus similar to 200 GPa, a Poisson ratio similar to 0.27, and a coefficient of thermal expansion similar to $2.3 \times 10^{-6}/°$ C. One skilled in the art of microfabrication will understand that the mechanical properties of silicon nitride thin films can vary depending on deposition conditions and stoichiometry, and that other mechanical properties could be contemplated that would yield similar behavior. The flexible membrane 202 diameter is 500 µm and the flexible membrane 202 thickness is 0.5 The sealed cavity 203 contains a vacuum. The substrate member 200 and the spacer member 201 consist of silicon with a coefficient of thermal expansion of $2.6 \times 10^{-6}/°$ C. The spacer member is greater than 11 µm thick. The illumination wavelength is 800 nm. At a normal intraocular pressure of 15 mmHg (735 mmHg absolute pressure at sea level) the pressure measurement error with change in temperature is similar to 0.12 mmHg/° C. This restricts the measurement error to less than ±0.25 mmHg under the anterior chamber temperature fluctuations described above. In an embodiment, the intraocular pressure measurement system 100 indicates the pressure measurement is potentially erroneous if extreme ambient temperatures are detected. In an embodiment, the pressure sensor 101 is calibrated for extreme ambient temperatures. Other dimensions and materials could be contemplated that also reduce temperature dependence to acceptable levels.

In a preferred embodiment an intraocular pressure sensor 101 has a spacer member 201 with a thickness that provides an interference pattern 300 without using a light source that relies on laser action. The coherence length of the incident light 103 must be longer than twice the thickness of the sealed cavity 203. The spacer member 201 has a thickness that ensures the separation of the flexible membrane 202 and the substrate member 200 is less than half the coherence length of the incident light 103. Laser light sources typically have coherence lengths of greater than 1 mm. However, eye safety concerns when using lasers indicate that a light emitting diode light source is preferred. Light emitting diodes have coherence lengths ranging from approximately 1 μm to 1000 μm. In an embodiment, an optical filter 105 is used to further increase the coherence length of at least one of the incident light 103 or the resultant light 113. In an exemplary sensor the spacer member is less than 50 μm thick so that the separation between the flexible membrane 202 and the substrate member 200 does not exceed 50 um and thus an incident light 103 with a coherence length of less than 25 μm can be used to form the interference pattern 300. For an infrared light source 102 with a center wavelength of 800 nm this corresponds to a spectral bandwidth of approximately 25 nm. Other dimensions could be contemplated that also allow light sources 102 not employing laser action to be used. One skilled in the art of interferometry will understand that there are subtle differences in definition of coherence length and spectral bandwidth depending on the spectral shape of the light, the criterion for bandwidth, and the criterion for coherence. As such, one skilled in the art will understand that the numbers given are representative and that other criteria for coherence length could be conceived.

In one embodiment, shown in FIG. 2B, the intraocular pressure sensor 101 further comprises one or more layers 204 of additional material coated on the external side of the flexible membrane 202. This additional material has refractive index and thickness such that reflection from the membrane 202 is substantially equal to the reflection from the substrate member 200. Equalizing the reflection from the membrane 202 and substrate member 200 provides the greatest interference pattern 300 visibility, where visibility is defined as the ratio of the differences in the maximum and minimum intensity in the interference pattern 300 to the sum of the maximum and minimum intensity. As a result, the signal to noise ratio of the captured interference pattern 300 will be maximized if all other conditions are equal. It is important to note that for certain combinations of flexible membrane 202 thickness and refractive index the additional layer 204 is unnecessary because the reflection is intrinsically balanced. However, the thickness of the flexible membrane 202 is often determined by the pressure range and sensitivity required, and cannot be freely adjusted based on optical considerations. In an exemplary intraocular pressure sensor 101 the substrate member 200 is silicon with refractive index similar to 3.7, the flexible membrane 202 is low stress silicon nitride with refractive index similar to 2.2 and thickness similar 350 nm, the additional layer 204 is one of several poly(p-xylylene) polymers with a refractive index similar to 1.6 and a thickness similar to 150 nm, and the illumination wavelength is similar to 800 nm. In this example the interference pattern 300 visibility improves from 0.48 without the additional layer 204 to 0.75 with the additional layer 204 in place. Other materials with different refractive indices and thicknesses could be conceived to achieve a similar improvement.

In the case of a single intraocular pressure sensor 101 illuminated by a single wavelength of light, the phase change of the interference pattern 300 is restricted to the less than 2n over the range of pressures to be measured. In an exemplary sensor the flexible membrane diameter is 300 μm and the flexible membrane thickness is 1.5 The wavelength of illumination is 800 nm. Over a range of absolute pressures from 610 mmHg to 820 mmHg the sensor's 101 sensitivity is similar to 0.02 radians/mmHg and the interference pattern 300 undergoes a phase change of less than 2π. As a result, there is no ambiguity in the pressure measurements between 610 mmHg and 820 mmHg. Other dimensions and materials for the flexible membrane 202 could be contemplated that also restrict the phase change to 2n over a desired pressure range.

In the embodiment shown in FIG. 7A, the intraocular pressure sensor 101 further comprises a coating 700 containing a fluorescent material on the substrate member 200. A light source 102 excites the fluorescent material of the coating 700 and the fluorescent material of the coating emits a light of a different second wavelength. The proximity of the flexible membrane 202 to the substrate member 200 modulates the intensity of the emitted light of a different second wavelength and the detected intensity of the emitted light of the different second wavelength is used to determine the pressure. The coating 700 can be any material that is intrinsically fluorescent or that has been dyed with a fluorescent component. An example coating could be a polymer, such as poly-methyl methacrylate (PMMA), dyed with fluoresecent molecules, such as the near-infrared polymethine dyes. In an embodiment both the polymer and the dye are be transparent in the visible part of the spectrum for aesthetic reasons. In an embodiment, both excitation and emission wavelengths are in the near infrared to prevent the patient from seeing the incident light 103 or resultant light 113 while the pressure is being measured. In another embodiment shown in FIG. 7B, the intraocular pressure sensor 101 further comprises a coating 700 containing a fluorescent material on the flexible membrane 202.

The intensity of the resultant light 113 from the pressure sensor 101 is modulated based on several phenomena. First the intensity of incident light 103 that reaches the fluorescent coating 700 is modulated. This occurs because of wave optical effects typically described in terms of (1) interference of optical reflections from the membrane surfaces, the fluorescent material surfaces, and the substrate and (2) optical near-field and evanescent coupling across the sealed cavity when the separation of the membrane and substrate are on the order of the wavelength of light. When light is transmitted through two or more partially reflective surfaces it can interfere constructively and destructively depending on the separation of the surfaces. As a result, the transmitted power in the resultant light 103 depends on the separation of the surfaces. In the pressure sensor 101 there are at least four partially reflected surfaces: the two surfaces of the flexible membrane 202; the interface of the fluorescent coating 700 with the sealed cavity 203; and the interface of the substrate member 200 with the fluorescent coating 700. First, the transmission of incident light 103 to the fluorescent coating 700 is modulated by the separation between the flexible membrane 203, which is partially reflective, and the fluorescent coating 700 on the substrate member 200. As the transmitted power at the excitation wavelength changes, the light emission from the fluorescent coating 700 is modulated as well.

The same effects that modulate the intensity of incident light 103 reaching the fluorescent coating 700 also modulates the resultant light 113. In addition, a significant fraction of the light emitted by the fluorescent coating 700 is reflected back into the material by total internal reflection. If the refractive index of the fluorescent coating 700 is greater than the underlying substrate member 200, then this light is completely trapped in the fluorescent layer. In either case, the evanescent electric field from the internally reflected light extends a short distance beyond the interface between the fluorescent coating 700 and the sealed cavity 203. If the flexible membrane 203 is sufficiently close to the fluorescent coating 700 (separation similar to wavelength) then light that would otherwise be totally internally reflected in the fluorescent coating 700 will couple into the flexible membrane 202. The strength of this coupling is strongly dependent on the separation of the two layers; thus, a change in pressure that deflects the flexible membrane 202, alters the fluorescent membrane 202-fluorescent coating 700 separation, and the light emission. Moreover, light will be trapped in the flexible membrane 202 by total internal reflection.

In an exemplary pressure sensor 101, a substrate member 200 is coated with a fluorescent coating 700 with real refractive index 1.7 and that is sufficiently thick and absorbing to absorb all of the excitation light. A flexible membrane 202 is separated from the fluorescent coating 202 by a sealed cavity 203 containing vacuum. The pressure sensor 101 is excited with the incident light 113 at wavelength of 770 nm in the near infrared and the fluorescent coating 700 emits at 800 nm. For explanatory purposes, the incident light 103 is normally incident, unpolarized, and collimated, and the fluorescence yield (or quantum efficiency) is 1. The resultant light 113 emitted from the fluorescent coating 700 is unpolarized and has a diffuse (Lambertian) distribution.

Figure 11A:
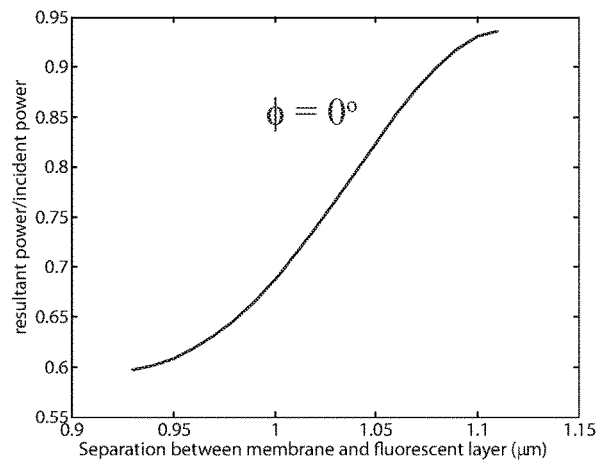
FIG. 11A through FIG. 11D are graphs showing a calculated ratio of resultant light power to incident light power as a function of membrane-fluorescent coating separation.

FIG. 11A shows a calculated ratio of resultant light 113 power to incident light 103 power as a function of membrane 202-fluorescent coating 700 separation. This ratio is a direct measure of membrane 202 deflection and thus a measure of pressure.

The pressure sensor 101 need not operate with collimated incident light 103 or with normally incident light 103. However, the output of the pressure sensor 101 is dependent on the angle of illumination, $\phi$.

Figure 11B:
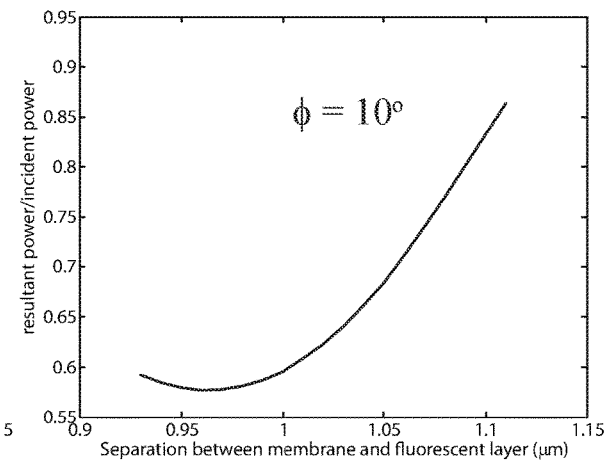

FIG. 11B shows a calculated ratio of resultant light 113 power to incident light 103 power as a function of membrane 202-fluorescent coating 700 separation with an illumination angle of 10 degrees from normal. The relationship is different and this angle dependence must either be calibrated out of the pressure reading or eliminated by a more sophisticated sensor design described in more detail below.

Figure 7C:
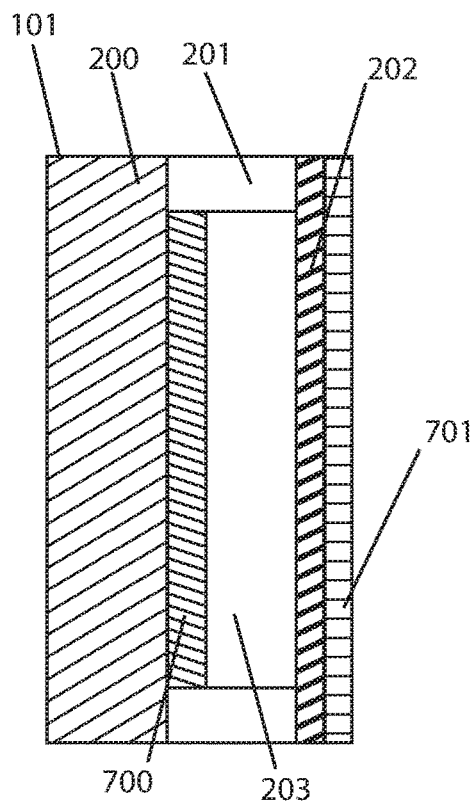

In an embodiment shown in FIG. 7C, the flexible membrane 203 is also coated with a scattering medium 701 on the side of the membrane external to the sealed cavity 203 to enhance light emission from the sensor 101 and minimize illumination angle dependence, as further described below. An example of such a scattering medium is polytetrafluoroethylene. Modulation of the incident light 103 reaching the fluorescent layer and modulation of the resultant light 113 exiting the sensor are both governed by the phenomena described above. The scattering medium 701 serves two purposes. First the scattering medium 701 randomizes the angle of incident light 103 to reduce output dependence on the angle of illumination. Secondly, the scattering medium 701 serves to extract light from the flexible membrane 202 and the fluorescent coating 700 that would otherwise be trapped by total internal reflection. This both increases the total amount of light emitted by the sensor and alters the relationship between the amount of resultant light 113 and the flexible membrane 202—fluorescent coating 700 gap.

Figure 7D:
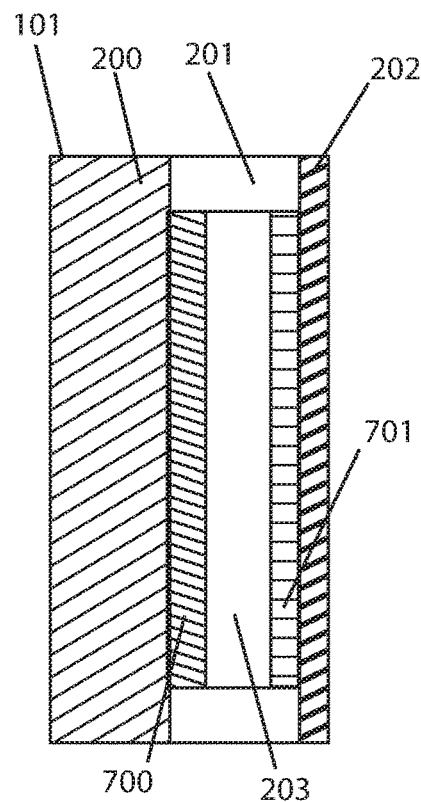

In an alternative embodiment, shown in FIG. 7D, the scattering medium 701 is placed on the surface of the flexible membrane 202 inside the sealed cavity 203. This configuration can improve light extraction from the fluorescent material because the scattering medium 701 is in a region of greater evanescent electric field strength.

In an exemplary sensor a scattering medium 701 is coated on the flexible membrane 202 surface external to the sealed cavity 203. Both incident light 103 and emitted light are diffusely (Lambertian) scattered at the membrane surface. As a result, the ratio of incident light 103 power to resultant light 113 power is no longer dependent on angle of illumination. However, the angle of illumination will affect the total input power coupled into to the sensor.

Figure 11C:
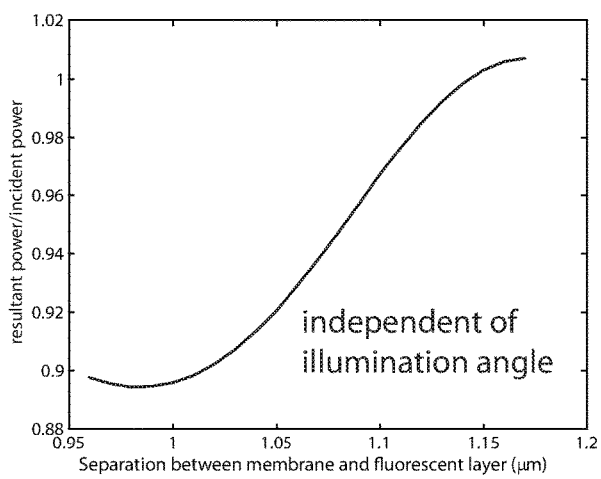

FIG. 11C plots the calculated ratio of resultant light 113 power to incident light 103 power as a function of flexible membrane 202-fluorescent coating 700 separation with the scattering medium 701 on the external side of the flexible membrane 202. This relationship is independent of illumination angle.

In an embodiment, the fluorescent coating 700 is placed in the flexible membrane 202, rather than on the substrate member 200, as shown in FIG. 7B. This embodiment is governed by the same phenomena; however, interference effects, near field effects, and evanescent coupling are all modified by the position of the fluorescent coating 700 in relation to the other sensor components. Specifically, light is trapped in the combined structure of the fluorescent coating 700 and the flexible membrane 202, and is evanescently coupled to the substrate member 200 depending on the fluorescent coating 700—substrate member 200 separation.

In another embodiment of the exemplary intraocular pressure sensor 101, two different fluorophors are contained in the fluorescent coating 700, and the two fluorophors emit light at two different wavelengths. The detector 106 measures the ratio of optical power at the two different wavelengths. In an embodiment the detector comprises a dichroic beam splitter and two light sensors. Each light sensor detects only one wavelength. In another embodiment, the detector comprises a beam splitter, two optical filters, and two light sensors. Again, each light sensor detects only one wavelength. By measuring the difference in detected optical power between the two sensors, the pressure measurement system 101 can compensate for different excitation and emission efficiencies that occur when the eye moves relative to the light source 102 and the detector 106 during or between measurements.

In an exemplary sensor 101 the fluorescent coating 700 emits at two wavelengths, 800 nm and 900 nm. When both fluorophors are excited, the ratio of the detected intensity between the two wavelengths corresponds to intraocular pressure. In this way we need not know the excitation power for any given measurements.

Figure 11D:
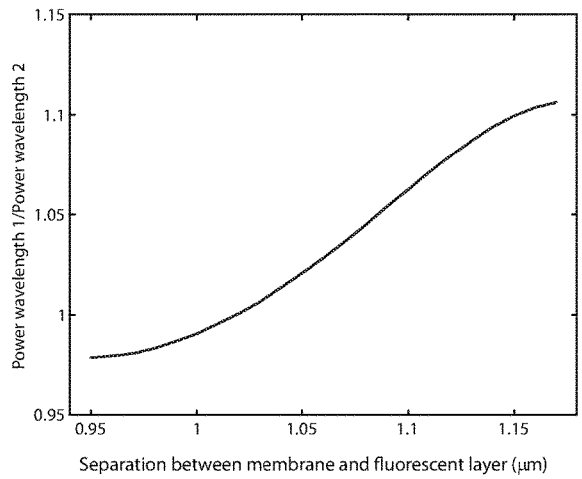

FIG. 11D plots the ratio of light detected at 800 nm to that detected at 900 nm as a function of the flexible membrane 202—fluorescent coating 700 separation.

As shown in FIG. 12, an exemplary method 1200 for determination of intraocular pressure, includes the steps of: S1202 placing an intraocular pressure sensor 101 (FIG. 1) in an eye (e.g., eye 505 of FIG. 5B), the intraocular pressure sensor 101 including a substrate member 200, a spacer member 201, and a flexible membrane 202, the substrate member 200, the spacer member 201 and the flexible membrane 202 defining a sealed cavity 203 wherein the flexible membrane 202 moves and/or deforms in response to intraocular pressure changes; S1204 illuminating, with a light source 102, the intraocular pressure sensor 101 with one or more wavelengths of light; and S1206 detecting, with a detector, a resultant light that contains information about intraocular pressure.

In an embodiment, the flexible membrane 202 (FIG. 2) both transmits and reflects the one or more wavelengths of light, the substrate member 200 reflects the one or more wavelengths of light transmitted by the flexible membrane 202, the light reflected by the substrate member 200 interferes with light reflected from the flexible membrane 202 to create an interference pattern 300, and the interference pattern 300 corresponds to intraocular pressure.

In an embodiment, the step S1206 detecting the resultant light includes capturing, with an electronic imaging device, an image of the interference pattern 300, and the method further comprises a step S1208 performing a phase calculation on the image of the interference pattern 300 to determine phase angles of the interference pattern 300; and a step S1210 correlating the phase angles with intraocular pressure.

In an embodiment, the method further comprises a step S1212 positioning an optical filter 105 between the intraocular pressure sensor 101 and at least one of the light source 102 and the electronic imaging device, the optical filter 105 providing an optical coherence length greater than twice the distance from the flexible membrane 202 to the substrate member 200.

In an embodiment, the step of S1204 illuminating the intraocular pressure sensor includes modulating the light source 102 in time to allow for lock-in detection of the interference pattern 300 by the electronic imaging device.

In an embodiment, the method further comprises a step S1214 coating a coating 700 containing fluorescent material on at least one of the substrate member 200 and the flexible membrane 202, wherein the step S1204, illuminating the intraocular pressure sensor, includes exciting the fluorescent material of the coating 700 with a light source 102 such that the fluorescent material of the coating 700 emits a light of a different second wavelength, the emission of the light of the second wavelength being the result of excitation of the fluorescent material, wherein the proximity of the flexible membrane 202 to the substrate member 200 modulates the intensity of the resultant light 113 of a different second wavelength, and wherein the step S1206 detecting the resultant light, includes detecting an intensity of the resultant light 113 of the different second wavelength to determine the pressure.

In an embodiment, the step S1202, placing the intraocular pressure sensor in an eye, further includes immobilizing the intraocular pressure sensor 101 in the eye 505 using an anchoring member 500 attached to the intraocular pressure sensor 101.

In an embodiment, the anchoring member 500 comprises a plate 502 and an arm 503, and immobilizing the intraocular pressure sensor 101 further includes inserting the plate 502 into a scleral pocket of the eye 505; and inserting the arm 503 into an anterior chamber 506 of the eye through a scleral tunnel.

In an embodiment, immobilizing the intraocular pressure sensor in the eye further includes suturing the plate 502 to the eye using holes 504 in the plate 502.

Figure 13:
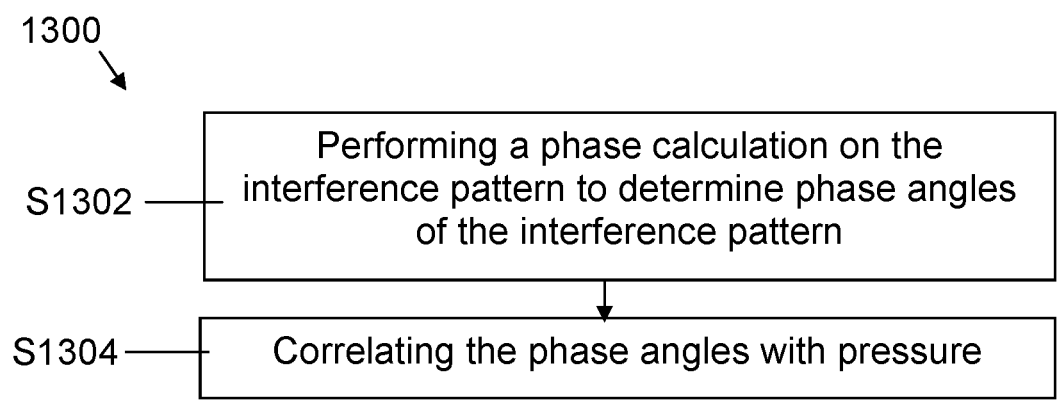
FIG. 13 is a flowchart of an exemplary method for the determination of pressure from an interference pattern produced by an intraocular pressure sensor according to the invention.

As shown in FIG. 13, an exemplary method 1300 for the determination of pressure from an interference pattern 300 produced by an intraocular pressure sensor 101 comprising a substrate member 200; a spacer member 201; and a flexible membrane 202; the substrate member 200, the spacer member 201 and the flexible membrane 202 defining a sealed cavity 203; wherein the flexible membrane 202 moves and/or deforms in response to intraocular pressure changes and the movement or deformation of the flexible membrane 202 is measured optically, wherein light from a light source 102, emitting one or more wavelengths of light either simultaneously or sequentially, is both transmitted and reflected by the flexible membrane 202, and reflected by the substrate member 200, and wherein the light reflected by the substrate member 200 interferes with light reflected from the flexible membrane 202 to create an interference pattern 300, the method includes the steps of: S1302 performing, by a processing device 107, a phase calculation on the interference pattern 300 to determine phase angles of the interference pattern 300; and S1304 correlating the phase angles with pressure.

An exemplary interference pattern 300 has intensity, I, that is periodic with the square of the spatial variables. An exemplary signal of this type is $I(x,y)=A\cos(k_x x^2 + k_y y^2)+B$ where A is the amplitude of the fringe modulation, $k_x$ and $k_y$ are the spatial frequencies of the rings in the x- and y-directions, x and y are the spatial coordinates across the sensor surface, and B is constant offset of zero light level. In practice, this signal may be discretely sampled by an electronic imaging device so that the pixel value at the $j^{th},k^{th}$ location in the image matrix is given by $I_{jk}=A\cos(k_x x_j^2 + k_y y_k^2)+B$.

To determine the phase of the interference pattern 300, the two-dimensional image is multiplied by a kernel of the form $K(k_x,k_y,x,y)=\exp[-ik_x x^2 - ik_y y^2]$. For each value of $k_x$ and $k_y$, the product of the signal and kernel is integrated over x and y to yield the integral transform given by $F(k_x,k_y)=\iint I(x,y)\exp[-jk_x x^2 - jk_y y^2]dxdy$. FIG. 3B shows the absolute value of the integral transform 302, $|F(k_x,k_y)|$. As can be seen in FIG. 3B, there is a peak value 301 in $|F(k_x,k_y)|$ at a particular non-zero pair of values for $k_x$ and $k_y$. At this peak value 301, the phase angle of the transform, $$\phi(k_x, k_y) = \arctan\left(\frac{\text{Im}\{F(k_x, k_y)\}}{\text{Re}\{F(k_x, k_y)\}}\right),$$

will relate to how the rings are spatially positioned. Because the spatial position of the rings in the interference pattern 300 is related to the deflection of the flexible membrane 202 with respect to the substrate member 200, one can determine intraocular pressure from the phase of the transform at the spatial frequencies corresponding to the peak 301. A change in the phase of the transform indicates a shift in position of the rings and thus a change in pressure. In an embodiment, the transform is computed discretely and becomes $$F(k_x, k_y) = \sum_{j=0}^{N}\sum_{k=0}^{M} I_{jk}\exp[-ik_x x_j^2 - ik_y y_k^2]$$

where N is the number of pixels in the x-direction and M is the number of pixels in the y-direction.

In an embodiment, the spatial frequencies are known and the transform need only be computed for one value of $k_x$ and one value of $k_y$. In an embodiment, the spatial frequencies are not known, and the integral transform is computed for a range of spatial frequencies, the peak 301 in the absolute value of the integral transform 302 is identified, and the phase is computed at the spatial frequencies corresponding to the peak 301.

FIG. 3C plots the phase at the peak 301 of $|F(k_x,k_y)|$ as a function of pressure for experimentally obtained data. The sensor was placed in a sealed chamber with water around it, and the pressure was varied with a syringe. The pressure values on the abscissa were measured with a commercial analog pressure sensor placed in the same test chamber as the optical sensor. It is apparent that phase is correlated with pressure, and that the sensor covers a range of physiologically relevant pressures found in the human eye (5-30 mmHg). In addition, this sensor design covers this range of pressures relative to atmospheric pressure without exceeding a phase change of 2π and there is no ambiguity in the phase-pressure relationship.

In an embodiment, the normal axis of the intraocular pressure sensor 101 is not required to be coincident with the optical axis of at least one of the light source 102 and detector 106. The interference pattern 300 is spatially compressed along the direction associated with the tilt angle of the sensor 101. For example, if the patient looks to the side during a pressure measurement, the sensor 101 will rotate about the y-axis and the interference pattern 300 will appear to compress in the x-direction. Compression of the interference pattern 300 in space shifts the peak 301 in $|F(k_x,k_y)|$ to a higher spatial frequency. Thus, one can determine the angle of the sensor 101 with respect to the optical axis of the readout system from the values of $k_x$ and $k_y$. This allows one to correct for any error that would otherwise be introduced by the patient not looking directly along the optical readout axis. FIG. 4A shows an interference pattern 300 with the sensor rotated by 25 degrees about its y-axis. This rotation is extreme, but is used for exemplary purposes to make the fringe compression appear clear by visual inspection. FIG. 4B shows the absolute value of the integral transform 302, $|F(k_x,k_y)|$. In this case, the peak 301 shifts to higher values of $k_x$ because of the rotation.

Figure 9C:
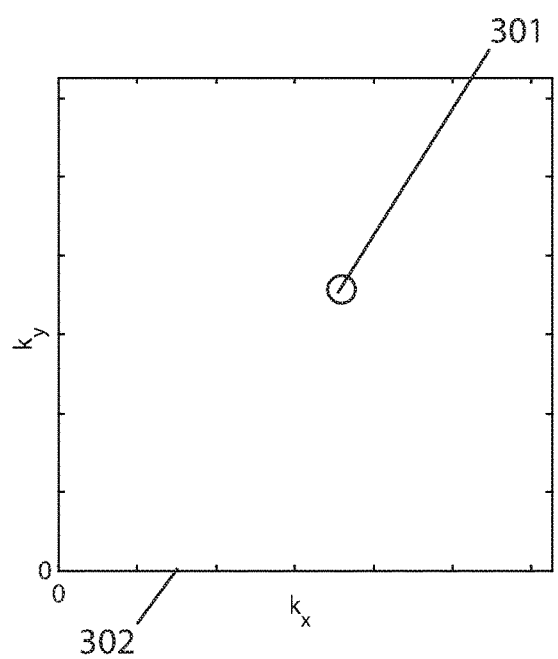
FIG. 9C and FIG. 9D are graphs of the absolute value of integral transforms of the interference patterns of FIG. 9A and FIG. 9B, respectively.
Figure 9D:
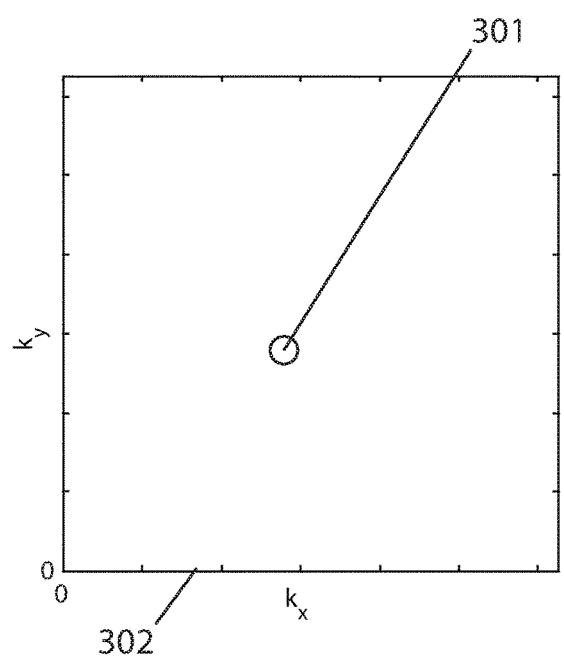

In an embodiment, at least one of a larger range of pressures needs to be measured or greater sensitivity, i.e. phase change with change in pressure, is required. Two wavelengths of light illuminate the sensor 101. In an embodiment, the wavelengths illuminate the sensor sequentially so the interference pattern 300 from each wavelength is measured separately. FIG. 9A and FIG. 9B show two interference patterns 300 for sequential measurement of a sensor with wavelengths of 700 nm and 900 nm respectively. FIG. 9C and FIG. 9D show the absolute value of the integral transforms 302 for 700 nm and 900 nm wavelengths respectively. The peak values 301 occur at different spatial frequencies for the two different wavelengths. Calculating the phase at the spatial frequencies corresponding to each peak 301 in each transform allow unambiguous determination of the pressure even if the phase change of one or both interference patterns 300 exceeds 2π.

Figure 10B:
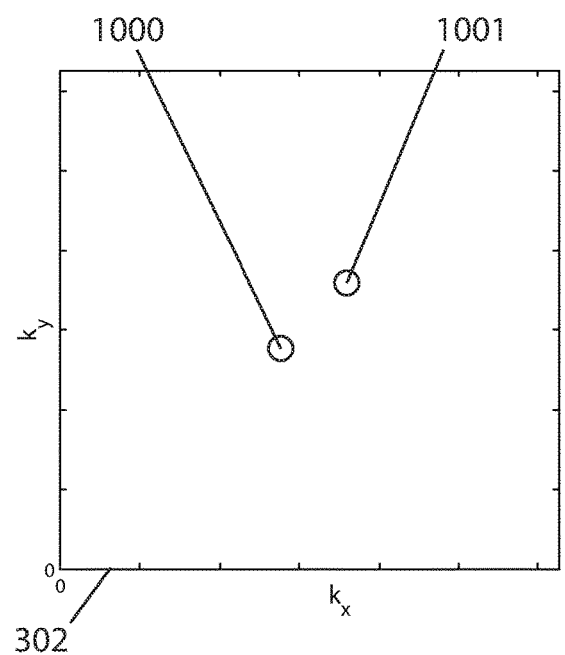
FIG. 10B is a graph of the absolute value of the integral transform of the interference pattern of FIG. 10A.

In an embodiment, the two wavelengths illuminate the sensor simultaneously, and a single interference pattern 300 is captured by the detector 106. FIG. 10A shows the interference pattern 300 and FIG. 10B shows the absolute value of its integral transform 302 when the sensor is simultaneously illuminated with wavelengths of 700 nm and 900 nm. In this case the two wavelengths result in a peak 1000 for 900 nm and a peak 1001 for 700 nm in a single integral transform. The shorter wavelength yields a higher spatial frequency. The two phases associated with the two wavelengths can be used to track phase changes larger than 2π without ambiguity in the relationship between phase and pressure. This method can increase the dynamic range of a sensor or allow a certain dynamic range to be maintained while redesigning the sensor for greater sensitivity.

Thus, the invention provides systems, devices, and methods for measuring intraocular pressure. One of ordinary skill in the art will recognize that additional steps and configurations are possible without departing from the teachings of the invention. This detailed description, and particularly the specific details of the exemplary embodiment disclosed, is given primarily for clearness of understanding and no unnecessary limitations are to be understood therefrom, for modifications will become evident to those skilled in the art upon reading this disclosure and may be made without departing from the spirit or scope of the claimed invention.

What is claimed is:

1. A system for determination of intraocular pressure, the system comprising:
    an intraocular pressure sensor including a substrate member, a spacer member, and a flexible membrane, the substrate member, the spacer member and the flexible membrane forming walls of a sealed cavity having no openings for fluid communication with a vacuum, the flexible membrane having an exterior surface and being configured to deform in response to intraocular pressure when the intraocular pressure sensor is implanted in an eye;
    a light source configured to illuminate the exterior surface of the flexible membrane with an incident light including one or more wavelengths of light;
    the flexible membrane configured to partially transmit and partially reflect the incident light, the substrate member configured to reflect the incident light that is partially transmitted back through the flexible membrane to create an interference pattern with the incident light that is partially reflected, the interference pattern consisting of bright and dark rings having a separation depending on a curvature of the flexible membrane; and
    an electronic imaging device configured to capture an image of the interference pattern.

2. The system of claim 1, further comprising a processing device in communication with the electronic imaging device,
    wherein the processing device performs a phase calculation on the image of the interference pattern to determine phase angles of the interference pattern, and correlates the phase angles with intraocular pressure.

3. The system of claim 2, wherein the processing device further performs the phase calculation using an integral transform and calculates the phases at one or more spatial frequencies corresponding to peaks in an absolute value of the integral transform.

4. The system of claim 3, wherein the processing device uses the values of the spatial frequencies corresponding to peaks in the absolute value of the integral transform to correct for errors which arise from angular deviation of a sensor normal from an optical axis of a readout system.

5. The system of claim 2, wherein each wavelength emitted by the light source has a coherence length longer than the twice the separation between the flexible membrane and the substrate member.

6. The system of claim 2, further comprising an optical filter positioned between the intraocular pressure sensor and at least one of the light source and the electronic imaging device, and providing an optical coherence length greater than twice the distance from the flexible membrane to the substrate member.

7. The system of claim 2, wherein the light source is modulated in time to allow for lock-in detection of the interference pattern.

8. The system of claim 2, wherein the light source emits multiple wavelengths of light, either simultaneously or sequentially, and wherein the dimensions of the flexible membrane allow a phase change in the interference pattern of greater than $2\pi$ for at least one of the multiple wavelengths of light.

9. The system of claim 1, further comprising an anchoring member including an arm, the intraocular pressure sensor positioned on the arm, and a second intraocular pressure sensor positioned on the arm and having at least one of a different diameter, shape, membrane thickness, membrane material, and substrate material, the intraocular pressure sensor and the second intraocular pressure sensor providing at least one of redundant pressure measurement, failure detection, compensation for temperature fluctuations in the eye, increased pressure measurement sensitivity, and increased pressure measurement dynamic range.

10. The system of claim 1, further comprising an anchoring member including an arm, the intraocular pressure sensor positioned on the arm, and a second intraocular pressure sensor positioned on the arm and configured to provide redundant pressure measurements that increase confidence in the pressure reported by the system and to serve as an indication of failure if one of the intraocular pressure sensor and the second intraocular pressure sensor fails.

11. A device for measuring intraocular pressure comprising:
an intraocular pressure sensor including a substrate member, a spacer member, and a flexible membrane, the substrate member, the spacer member and the flexible membrane forming walls of a sealed cavity having no openings for fluid communication with a vacuum, the flexible membrane having an exterior surface and being configured to deform in response to intraocular pressure-changes when the intraocular pressure sensor is implanted in an eye, the flexible membrane configured to partially transmit and partially reflect an incident light that is incident on the exterior surface of the flexible membrane, the substrate member configured to reflect the incident light that is partially transmitted back through the flexible membrane to create an interference pattern with the incident light that is partially reflected, the interference pattern consisting of bright and dark rings corresponding to the intraocular pressure;
an anchoring member attached to the intraocular pressure sensor for immobilizing the intraocular pressure sensor in the eye.

12. The device of claim 11, wherein the anchoring member comprises a plate for insertion in a scleral pocket and for immobilizing the device, and an arm for entering an anterior chamber of the eye through a scleral tunnel.

13. The device of claim 12, wherein the plate includes holes for suturing the plate to the eye.

14. The device of claim 12, wherein the plate includes holes for assisting wound healing.

15. The device of claim 11, wherein the anchoring member comprises a pair of pincers to enclavate an iris of the eye.

16. The device of claim 11, wherein the anchoring member includes an arm, the intraocular pressure sensor positioned on the arm, further comprising a second intraocular pressure sensor positioned on the arm and having at least one of a different diameter, shape, membrane thickness, membrane material, and substrate material, the intraocular pressure sensor and the second intraocular pressure sensor providing at least one of redundant pressure measurement, failure detection, compensation for temperature fluctuations in the eye, increased pressure measurement sensitivity, and increased pressure measurement dynamic range.

17. The device of claim 11, wherein the anchoring member is formed from a biocompatible material selected from a group consisting of polymethylmethacrylate, silicone, biocompatible metals, and biocompatible metal alloys.

18. The device of claim 11, wherein the anchoring member includes an arm, the intraocular pressure sensor positioned on the arm, further comprising a second intraocular pressure sensor positioned on the arm and configured to provide redundant pressure measurements that increase confidence in the pressure reported by the system and to serve as an indication of failure if one of the intraocular pressure sensor and the second intraocular pressure sensor fails.

19. The device of claim 11, further comprising a protective member attached to the anchoring member and covering the intraocular pressure sensor to prevent contact between the flexible membrane and portions of the eye.

20. The device of claim 19, wherein the protective member is formed from a biocompatible material selected from a group consisting of polymethylmethacrylate, silicone, biocompatible metals, and biocompatible metal alloys.

* * * * *